(12) United States Patent
Gao et al.

(10) Patent No.: US 7,553,958 B2
(45) Date of Patent: Jun. 30, 2009

(54) LINKERS AND CO-COUPLING AGENTS FOR OPTIMIZATION OF OLIGONUCLEOTIDE SYNTHESIS AND PURIFICATION ON SOLID SUPPORTS

(75) Inventors: Xiaolian Gao, Houston, TX (US); Hua Zhang, Houston, TX (US); Peilin Yu, Houston, TX (US); Eric Leproust, Campbell, CA (US); Jean Philippe Pellois, New York, NY (US); Qin Xiang, Houston, TX (US); Xiaochuan Zhou, Houston, TX (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/726,269

(22) Filed: Mar. 21, 2007

(65) Prior Publication Data

US 2007/0287832 A1 Dec. 13, 2007

Related U.S. Application Data

(62) Division of application No. 10/099,382, filed on Mar. 13, 2002, now Pat. No. 7,211,654.

(60) Provisional application No. 60/275,666, filed on Mar. 14, 2001.

(51) Int. Cl.
C07H 21/00 (2006.01)
C07H 21/02 (2006.01)
C12Q 1/68 (2006.01)

(52) U.S. Cl. .................... 536/25.3; 536/23.1; 536/25.4; 435/6

(58) Field of Classification Search ...................... 435/6; 536/23.1, 25.3, 25.4
See application file for complete search history.

(56) References Cited

U.S. PATENT DOCUMENTS

| | | | |
|---|---|---|---|
| 5,143,854 A | 9/1992 | Pirrung et al. ............... 436/518 |
| 5,393,877 A | 2/1995 | McLean et al. | |
| 5,401,837 A | 3/1995 | Nelson et al. ............. 536/25.32 |
| 5,424,186 A | 6/1995 | Fodor et al. ..................... 435/6 |
| 5,552,471 A | 9/1996 | Woo et al. .................... 524/494 |
| 5,585,481 A | 12/1996 | Arnold et al. ............. 536/25.33 |
| 5,623,049 A | 4/1997 | Lobbering et al. .......... 530/300 |
| 5,625,052 A | 4/1997 | Woo et al. .................. 536/25.34 |
| 5,656,741 A | 8/1997 | Chow et al. ................. 536/25.3 |
| 5,656,744 A | 8/1997 | Arnold et al. ............... 536/25.3 |
| 5,738,829 A | 4/1998 | Kempe ........................ 422/107 |
| 5,744,305 A | 4/1998 | Fodor et al. ..................... 435/6 |
| 5,750,672 A | 5/1998 | Kempe ..................... 536/25.31 |
| 5,869,696 A | 2/1999 | Reddy et al. ................. 548/564 |
| 5,919,523 A | 7/1999 | Sundberg et al. ............ 427/333 |
| 6,005,125 A | 12/1999 | Zhang et al. ................. 554/218 |
| 6,015,895 A | 1/2000 | Pon et al. .................... 536/25.3 |
| 6,031,091 A | 2/2000 | Arnold et al. ............. 536/25.34 |
| 6,043,353 A | 3/2000 | Pon et al. .................... 536/25.3 |
| 6,051,374 A | 4/2000 | Simons et al. ................... 435/5 |
| 6,090,934 A | 7/2000 | Kumar et al. ............... 536/25.3 |
| 6,465,175 B2 | 10/2002 | Horn et al. | |
| 2003/0186226 A1* | 10/2003 | Brennan et al. ................. 435/6 |

FOREIGN PATENT DOCUMENTS

| | | |
|---|---|---|
| WO | 85/01051 A | 3/1985 |
| WO | 95/01987 A | 1/1995 |
| WO | 97/40458 A | 10/1997 |
| WO | 99/42813 | 8/1999 |
| WO | 00/12524 | 3/2000 |
| WO | 00/46231 | 8/2000 |
| WO | 99/41007 | 8/2000 |
| WO | 2001/096357 A2 | 12/2001 |

OTHER PUBLICATIONS

Beaucage and Iyer, "Advances in Synthesis of Oligonucleotides by the Phosphoramidite Approach," *Tetradedron* 48(12):2223-2311 (1992).
Beaucage and Iyer, "The Functionalization of Oligonucleotides Via Phosphoramidite Derivatives," *Tetradedron* 49(10):1925-1963 (1993).
Bigley and Payling, "Reaction of Organoboranes with Neutral Hydrogen Peroxide." *J. Am. Chem. Soc.* (*B*) 1811-1818 (1970).
Crea and Horn, "Synthesis of Oligonucleotides on Cellulose by a Phosphotriester Method," *Nucleic Acids Research* 8(10):2331-2348 (1980).
de Bear et al., "A Universal Glass Support for Oligonucleotide Synthesis," *Nucleosides & Nucleotides* 6(5):821-830 (1987).
Doty et al., "Strand Separation and Specific Recombination in Deoxyribonucleic Acids:Physical Chemical Studies", *Proc.Nat. Acad.Sci., U.S.A.* 46:461-477 (1960).
Dugas and Penney, *Bioorganic Chemistry: A Chemical Approach to Enzyme Action*, pp. 54-92 (1981).
Ellman et al., "Combinatorial thinking in chemistry and biology," *Proc. Natl. Acad. Sci., USA* 94:2779-2782 (1997).

(Continued)

*Primary Examiner*—Jezia Riley
(74) *Attorney, Agent, or Firm*—Casimir Jones S.C.

(57) ABSTRACT

A method of modulation of synthesis capacity on and cleavage properties of synthetic oligomers from solid support is described. The method utilizes linker molecules attached to a solid surface and co-coupling agents that have similar reactivities to the coupling compounds with the surface functional groups. The preferred linker molecules provide an increased density of polymers and more resistance to cleavage from the support surface. The method is particularly useful for synthesis of oligonucleotides, oligonucleotides microarrays, peptides, and peptide microarrays. The stable linkers are also coupled to anchor molecules for synthesis of DNA oligonucleotides using on support purification, eliminating time-consuming chromatography and metal cation presence. Oligonucleotides thus obtained can be directly used for mass analysis, DNA amplification and ligation, hybridization, and many other applications.

19 Claims, 11 Drawing Sheets

OTHER PUBLICATIONS

Fromageot et al., "The Synthesis of Oligoribonucleotides-III. Monoacylation of Ribonucleosides and Derivatives Via Orthoester exchange," *Tetradedron* 23:2315-2331 (1967).

Fryxell et al., "Nucleophilic Displacements in Mixed Self-Assembled Monolayers," *Langmuir* 12:5064-5075 (1996).

Gao et al., "A flexible light-directed DNA chip synthesis gated by deprotection using solution photogenerated acids," *Nucleic Acids Res.* 29:4744-4750 (2001).

Gallop et al., "Perspective. Application of Combinatorial Technologies to drug Discovery. 1. Background and Peptide Combinatorial Libraries," *J. Med. Chem.* 37:1233-1251 (1994).

Gordon et al., "Perspective. Application of Combinatorial Technologies to drug Discovery. 2. Combinatorial Organic Synthesis, Library Screening Strategies, and Future Directions." *J. Med. Chem.* 37:1385-1401 (1994).

Heise et al., "Grafting of Polypeptides on Solid Substrates by Initiation of N-Carboxyanhydride Polymerization by Amino-Terminated Self-Assembled Monolayers," *Langmuir* 13:723-728 (1997).

Kowollik et al., "5'-O-methylthymidine," *Angew. Che. Interbat. Edit.* 5:735-736 (1966).

Lebl, M., "Perspective. Parrallel Personal Comments on "Classical" Papers in Combinatorial Chemistry," *J. Comb. Chem.* 1:3-24 (1999).

Marmur and Lane, "Strand Separation and Specific Recombination in Deoxyribonucleic Acids: Biological Studies", *Proc.Nat.Acad.Sci., U.S.A.* 46:453-461 (1960).

Merrifield, R.B., "Solid Phase Peptide Synthesis. I. The Synthesis of a Tetrapeptide," *J. Am. Chem. Soc.* 85:2149 (1962).

Netzer et al., "A New Apporach to Construction of Artificial monolayer Assemblies," *J. Am. Chem. Soc.* 105:674-676 (1983).

Netzer et al., "Adsorbed monolayers versus Langmuir-Blodgett monolayers-why and how? I. From monolayer to multilayer, by adsorption ," *J. Thin Solid Films* 99:67-76 (1983).

Netzer et al., "Adsorbed monlayers versus Langmuir-Blodgett monlayers-why and how? II. Characterization of built-up films constructed by stepwise adsorption of individual monolayers," *J. Thin Solid Films* 100:67-76 (1983).

Schwartz et al., "A Universal Adapter for Chemical Synthesis of DNA or RNA on Any Single Type of Solis Support," *Tetrahedron Letters* 36(1):27-30 (1995).

Sekine et al. "Facile synthesis of 3'-O-methylthymidine and 3'-dexoythymidine and related deoxygenate thymidine derivative: A new method for selective deoxygenation of secondary hydroxy groups," *J. Org. Chem.* 55:924-928 (1990).

Spitzer et al., "Inhibition of deoxyribonucleases by phosphorothioate groups in oligodeoxyribonucleotides," *Nucleic Acids Res.* 16:11691-11704 (1988).

Stewart and Young, *Solid Phase Peptide Synthesis*, pp. 24-66 (1969).

Strobel et al., "Defining the chemical groups essential for *Tetrahymena* group 1 intron function by nucleotide analog interference mapping," *Proc. Natl. Acad. Sci., USA* 94:2903-2908 (1997).

Wasserman et al., Structure and reactivity of alkylsiloxane monolayers formed by reaction of alkytrichlorosilanes on silicon substrates, *Langmuir* 5:1074-1087 (1989).

Dorman et al., Synthesis of oligoedeoxynucleotides and oligodeoxynucleotide analogs using phosphoramidite intermediates, Tetrahedron, vol. 40, No. 1 , 1984, pp. 95-102, XP002451716.

Usman et al., Automated Chemical Synthesis Of Long Oligoribonucleotides Using 2'-O-Silylated Ribonucleoside 3'-O-Phosphoramidites On A Controlled-Pore Glass Support: Synthesis Of A 43-Nucleaotide Sequence Similar To The 3'-Half Molecule Of An *Escherichia coli* Formylmethionne TRNA, Journal of the American Chemical Society, American Chemical Society, Washington, DC, US, vol. 109, No. 25, Dec. 9, 1987, pp. 7845-7854, XP000673490.

* cited by examiner

R = OCH₃, OCH₂CH₃, isopropyl, CH₃, and other substitution groups

FR: Fluorescein

R = H, -PO$_2$, -P(N(ipr)$_2$)(OCH$_2$CH$_2$CN)

Terminator: 5'-MeO-T, 5'-Me-T

R$_1$ = OCH$_3$, CH$_3$, etc.
R$_2$ = -P(N(ipr)$_2$)(OCH$_2$CH$_2$CN),
  oligonucleotides, linkers, etc.

Anchor: 5'-U phosphoramidite

R = H, CH$_3$

Deprotection and cleavage of Oligonucleotide

LINKERS AND CO-COUPLING AGENTS FOR OPTIMIZATION OF OLIGONUCLEOTIDE SYNTHESIS AND PURIFICATION ON SOLID SUPPORTS

The present application is a Divisional application of U.S. patent application Ser. No. 10/099,382 filed Mar. 13, 2002 now U.S. Pat. No. 7,211,654, which claims priority to U.S. Provisional Patent Application No. 60/275,666 filed Mar. 14, 2001, each of which is hereby incorporated by reference in its entirety.

FIELD OF THE INVENTION

The instant disclosure pertains to a method for optimization of synthesis and purification of synthetic oligomers, such as oligonucleotides and peptides, on a solid support. In particular, the disclosure pertains to the use of linkers and co-coupling agents for synthesizing oligonucleotides in a controlled manner and for obtaining oligonucleotides of high quality using simple purification procedures. The method particularly relates to high throughput synthesis of oligonucleotides for a variety of applications.

BACKGROUND OF THE INVENTION

The growing importance of combinatorial synthesis has created a need for new resins and linkers having chemical and physical properties to accommodate a wide range of conditions, since success depends on the ability to synthesize diverse sets of molecules on solid supports and to then cleave those molecules from the supports cleanly and in good yield.

Parallel synthesis, miniaturized analysis and interrogation of libraries of molecules are being perceived as one the most promising approaches available to modern chemistry and biology (Gallop et al., (1994) *J. Med. Chem.* 37, 1233-1251; Gordon et al., (1994) *J. Med. Chem.* 37, 1385-1401; Ellman et al., (1997) *Proc. Natl. Acad. Sci. USA*, 94, 2779-2282; Lebl, M. (1999) *J. Comb. Chem.* 1, 3-24. Examples include applications in combinatorial synthesis and screening of pharmaceutical compounds, biomolecular assays, and gene analysis using oligonucleotide microarrays or DNA chips. A common platform for these micro-chemical and biological experiments is planar surfaces, such as those made from silicon-based materials or synthetic polymers. Among these, glass plates (e.g. microscope slides, which are borosilicate glass) are easily available, easy to handle, and commonly used.

Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. Several linkers have been described in the literature. Their value is constrained by the need to have sufficient stability to allow the steps of combinatorial synthesis under conditions that will not cleave the linker, while still being cleavable under at least one set of conditions that is not employed in the synthesis. For example, if an acid labile linker is employed, then the combinatorial synthesis must be restricted to reactions that do not require the presence of an acid of sufficient strength to endanger the integrity of the linker. This sort of balancing act often imposes serious constraints on the reactions that can be employed in preparing the library.

Accordingly, what needed in the art are improved reagents for facilitating the synthesis and purification of polymers on solid supports.

SUMMARY OF THE INVENTION

In some embodiments, the present invention provides a stable linker [and more particularly, a selectively cleavable linker, i.e. a linker that is cleavable under at least one set of chemical reaction conditions, while not being substantially cleaved (i.e. approximately 90% or greater remains uncleaved) under another set (or other sets) of reaction conditions] for polymer synthesis comprising a chemical moiety immobilized on a solid support and not substantially cleaved under polymer synthesis conditions, which may include chain growth and even removal of the protecting groups from the polymer chain. A linker group typically has two ends, wherein one of the ends comprises a substrate attaching group and wherein the other of the ends comprises a polymer attaching group, wherein the polymer attaching group is preferably covalently linked to an anchor moiety and the anchor group has an attaching group for polymer synthesis. The present invention is not limited to any particular linker group. Indeed, the use of a variety of linker groups is contemplated, including, but not limited to, alkyl, ether, polyether, alkyl amide groups or a combination of these groups. The present invention is not limited to the use of any particular alkyl group. Indeed, the use of a variety of alkyl groups is contemplated, including —$(CH_2)_n$—, wherein n is from about 4 to about 20. The use of a variety of ether and polyether groups is contemplated, including —$(OCH_2CH_2)_n$—, wherein n is from about 1 to about 20. The use of a variety of alkyl amide groups is contemplated, including —$(CH_2)_m$—C(O)NH—$(CH_2)_n$— and —$(OCH_2CH_2)_m$—C(O)NH—$(OCH_2CH_2)_n$—, wherein m and n can be the same or different and m and n are from about 1 to about 20. The use of a variety of amide groups having the linking units of alkyl or ether bonds is contemplated, including —$R_1$—C(O)NH—$R_2$—, wherein $R_1$ and $R_2$ are alkyl, ether, and polyether groups.

The present invention is not limited to the use of any particular substrate attaching group. Indeed, the use of a variety of substrate attaching groups is contemplated, including, but not limited to trichlorosilyl and trialkyloxysilyl functional groups. The present invention is not limited to the use of any particular polymer attaching group. Indeed, the use of a variety of polymer attaching groups is contemplated, including, but not limited to amine, hydroxyl, thiol, carboxylic acid, ester, amide, epoxide, isocyanate, and isothiocyanate groups.

In preferred embodiments of the present invention, the linker is covalently bound to a support. The present invention is not limited to any particular support. Indeed, the use of a variety of supports is contemplated, including, but not limited to polymerized Langmuir Blodgett film, functionalized glass, Si, Ge, GaAs, GaP, $SiO_2$, $SiN_4$, modified silicon, polyacrylamide, polytetrafluoroethylene, polyvinylidendiflouride, polystyrene, polycarbonate, and co-polymers.

The present invention is not limited to the use of any particular anchor moiety. Indeed, the use of a variety of anchor moieties is contemplated, including, but not limited to, those of the following 1,2-diol derivatives of structures shown below:

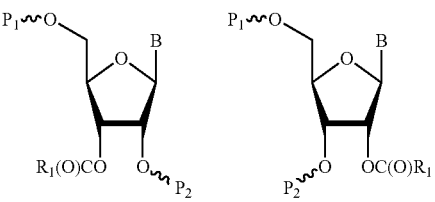

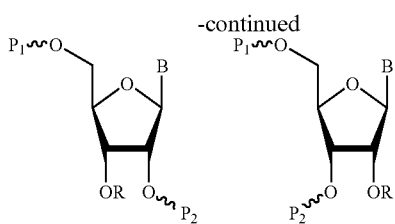

Wherein $P_1$ and $P_2$ are chain units comprised of polymer or linker and polymer; B is a nucleobase; $R_1$ are substitution groups, such as $CH_3$, $R_2Ph$ ($R_2$ are substitution groups on the phenyl ring, such as $SCH_3$, $Cl$, $NO_2$), $CH_2CH_2CN$. R is a protecting group, which is $OC(O)R_1$, t-butyldimethylsilyl (TBDMS), or other protecting groups used for 2'- or 3'-O protection of ribonucleotides. Once the protecting group is removed, the adjacent OH can accelerate the hydrolysis of the phosphodiester bond, resulting in cleavage of the polymer chain.

The present invention is not limited to the use of any particular anchor moiety. Indeed, the use of a variety of anchor moieties is contemplated, including, but not limited to, those of the 2'-deoxyuridine (dU) and abasic moiety of structures shown below:

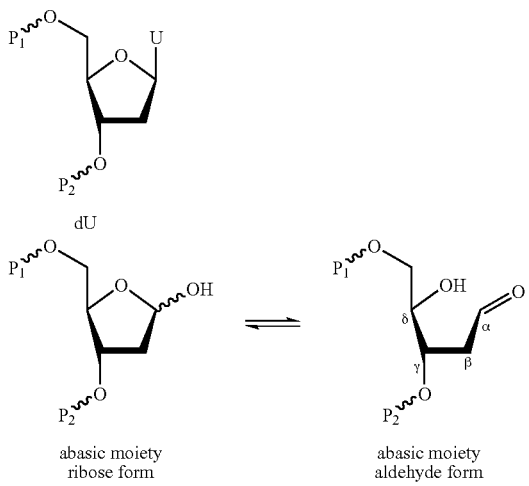

Wherein $P_1$ and $P_2$ are chain units comprised of linker and polymer or polymer; dU in an oligonucleotide that can be incorporated as its phosphoramidite and selectively cleaved by uracil-DNA glycosylase (UDG) (from *E. coli*), which catalyzes the removal of uracil from single- and double-stranded DNA. The apyriminic or the abasic sites formed by UNG are susceptible to cleavage by heat under alkaline conditions. The abasic moiety can be incorporated as its phosphoramidite monomer and is labile under basic conditions; treatment using amines, such as piperidine, EDA, and N,N'-dimethylethylenediamine causes β- or β- and δ-eliminations to give 5'-phosphate and 3'-phosphate or other 3'-products.

The present invention also includes anchor moieties of ribose nucleotides that can be incorporated in regular DNA synthesis using their phosphoramidites. These residues can be cleaved by ribonucleases, such as RNases A (cutting mostly pyrimidines), $T_1$ (cutting mostly G's) and $U_2$ (cutting mostly A's). The 3'- and 5'-ends of the cleaved sequences may require further modification using chemical and enzymatic conditions to obtain sequences with 3'- and 5'-functional groups required by the subsequent applications. There are many reactions conditions available for these modifications, including using 5'- or 3'-exonucleases for removal of terminal phosphate group.

The present invention is not limited to the use of any particular anchor moiety. Indeed, the use of a variety of anchor moieties is contemplated, including, but not limited to, those of the 2'-deoxyuridine (dU) and abasic moiety of structures shown below:

The present invention is not limited to the use of any particular anchor moiety. Indeed, the use of a variety of anchor moieties is contemplated, including, but not limited to, those of the modified nucleotides of structures shown below:

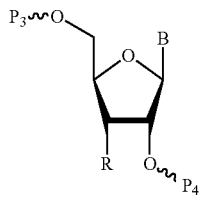

Wherein $P_3$ and $P_4$ are chain units comprised of polymer or linker and polymer; one or both P3 and P4 chains are linked to the nucleotide through thioate phosphate (PS) bonds. The PS bond forms in regular DNA or RNA chemical synthesis when the oxidation step employs either tetraethylthiuram disulfide (TETD) or 3H-1,2-bensodithiol-3-one 1,1-dioxide (BDTD) for sulfurizing phosphite trimesters formed from coupling of phosphoramidites (Spitzer, S.; Eckstein, F. (1988) Nucleic Acids. Res. 16, 11691-11704). The PS linkage can be selectively cleaved by the addition of $I_2$ (Strobel, S. A., and Shetty, K. Proc. Natl. Acad. Sci. USA. 94, 2903-2908).

In preferred embodiments, the anchor moiety is stable under conditions used for polymer synthesis, which may include conditions for chain growth as well as conditions for removal of the protecting groups from the polymer chain. The anchor moieties of the present invention may be cleavable under certain selected conditions. The present invention is not limited to any particular set of selective cleavage conditions. Indeed, the present invention contemplates that a variety of cleavage conditions may be utilized when appropriate, including 2-OH assisted 1-phosphate hydrolysis and enzymatic cleavage of the chemical bonds. In other embodiments of the present invention, the anchor moiety includes a polymer attaching group. In still further embodiments, a polymer is attached to the anchor moiety. The present invention is not limited to any particular polymer. Indeed, a variety of polymers are contemplated, including, but not limited to peptides and oligonucleotides.

The present invention is not limited to the use of any particular anchor moiety. Indeed, the use of a variety of anchor moieties is contemplated, including, but not limited to, those of the following structure:

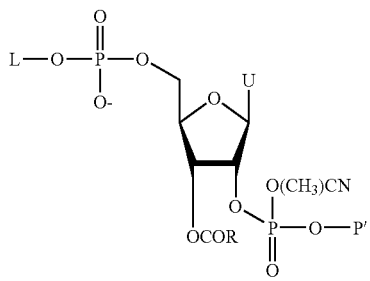

wherein L is the linker and P' is a polymer.

In still other embodiments, the present invention provides compounds possessing the structure:

Rs-L-Rp wherein $R_s$ is a substrate attaching group, $R_p$ is a polymer attaching group, and L is the linker.

The present invention is not limited to the use of any particular substrate attaching group ($R_s$). Indeed, the use of a variety of substrate attaching groups is contemplated, including, but not limited to chlorosilyl and alkyloxysilyl functional groups. The present invention is not limited to the use of any particular polymer attaching group. Indeed, the use of a variety of polymer attaching groups is contemplated, including, but not limited to amine, hydroxyl, thiol, carboxylic acid, ester, amide, epoxide, isocyanate, and isothiocyanate groups.

In some embodiments, $R_p$ is selected from the group including, but not limited to amine, hydroxyl, thiol, carboxylic acid, ester, amide, epoxide, isocyanate, and isothiocyanate groups.

In some embodiments of the present invention, the linker is covalently bound to a support. The present invention is not limited to any particular support. Indeed, the use of a variety of supports is contemplated, including, but not limited to polymerized Langmuir Blodgett film, functionalized glass, Si, Ge, GaAs, GaP, $SiO_2$, $SiN_4$, modified silicon, polyacrylamide, polytetrafluoroethylene, polyvinylidendiflouride, polystyrene, and polycarbonate.

In still further embodiments, the present invention provides methods for synthesizing oligonucleotides comprising: providing a substrate; a plurality of stable linkers; a plurality of anchor moieties; and nucleotide monomers; derivitizing the substrate with the plurality of stable linkers; attaching the anchor moieties to the stable linkers; and synthesizing oligonucleotides on the plurality of anchor moieties. In some embodiments, the methods further comprise deprotecting the oligonucleotides and selectively cleaving the oligonucleotides from the substrate by reacting the substrate under conditions such that the polymer is cleaved at the anchor moiety.

In still further embodiments, the present invention provides methods for controlling the number of oligonucleotides synthesized at a predetermined site on a substrate comprising: providing a substrate; a plurality of stable linkers; a plurality of anchor moieties; nucleotide monomers; and co-coupling agents; derivitizing the substrate with said plurality of stable linkers; attaching the anchor moieties to the stable linkers; and synthesizing a oligonucleotide on the plurality of anchor moieties from the monomers in the presence of the co-coupling agents under conditions such that at least a portion of the oligonucleotides are terminated.

In still other embodiments, the present invention provides methods of purifying oligonucleotides comprising: providing: a substrate comprising oligonucleotides attached to a substrate via an anchor moiety attached to a stable linker group, a deprotecting solution, and a wash solution; deprotecting said oligonucleotides with said deprotecting solution, washing said oligonucleotides attached to a substrate with said wash solution, and cleaving said oligonucleotides at said anchor group to provide purified oligonucleotides, wherein said purified oligonucleotides are characterized by the substantial absence of metal ions and/or other contaminants and said stable linker group remains attached to said substrate.

In still other embodiments, the present invention provides methods of obtaining purified oligonucleotides comprising: providing: a substrate comprising oligonucleotides attached to a substrate via an anchor moiety attached to a stable linker group, a deprotecting solution, a wash solution, and a cleavage solution; deprotecting said oligonucleotides with said deprotecting solution, washing said oligonucleotides attached to a substrate with said wash solution, and cleaving said oligonucleotide using said cleavage solution at said anchor group to provide purified oligonucleotides, wherein said purified oligonucleotides are characterized by the substantial absence of metal ions and said stable linker group remains attached to said substrate. The oligonucleotides thus obtained have many applications, such as substrates of nucleases, polymerases, kinases, or ligases, known to those of skilled in the art.

DEFINITIONS

Figure 1:
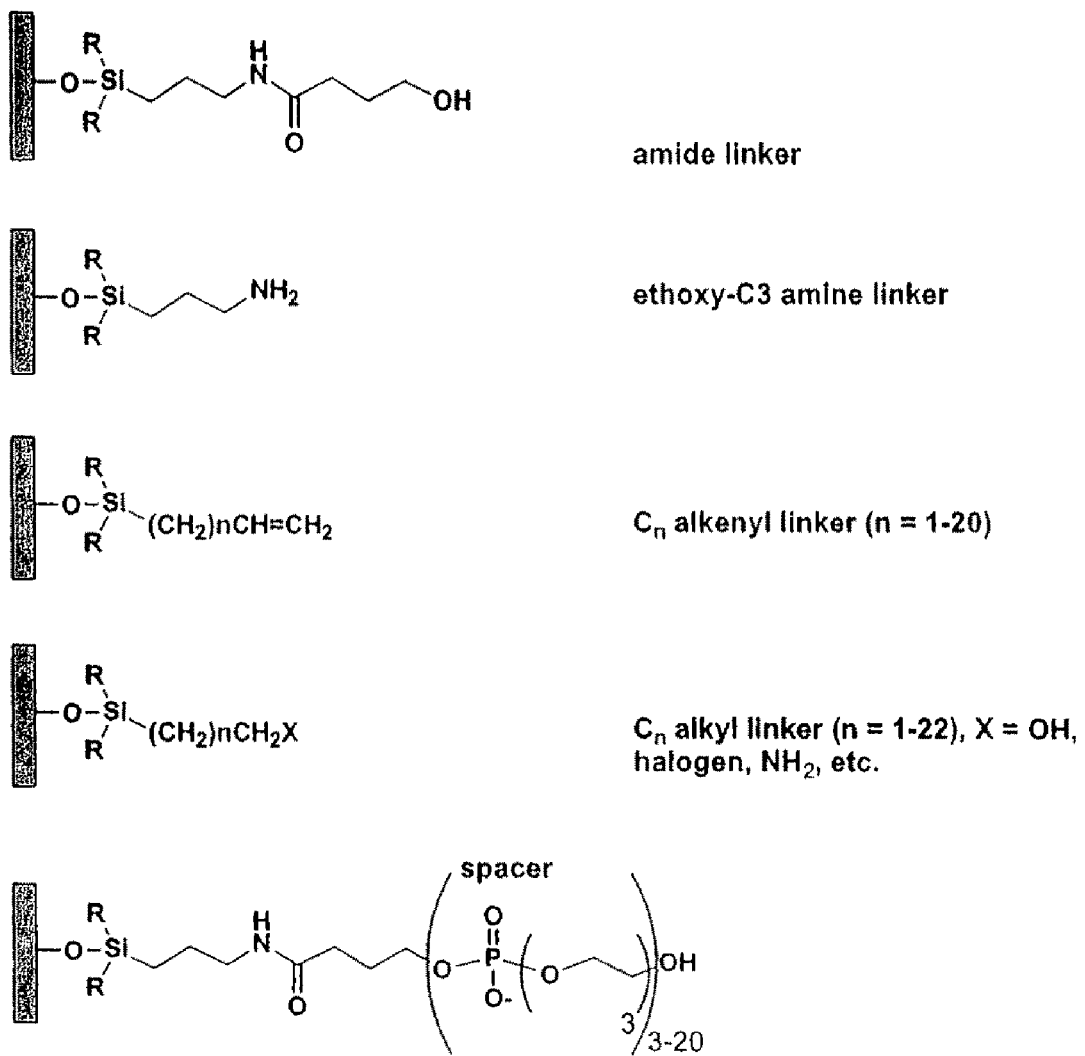
FIG. 1 provides examples of the chemical structure of the linker groups of the present invention attached to a solid substrate.

The following terms are intended to have the following general meaning as they are used herein:

The term "substrates" and "solid supports" are used interchangeably to refer to any material that is suitable for derivatization with a linker group. Examples of substrates include, but are not limited to glass, Si-based materials, functionalized polystyrene, functionalized polyethyleneglycol, functionalized organic polymers, nitrocellulose or nylon membranes, paper, cotton, and materials suitable for synthesis. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as oligonucleotides and peptides attached to solid supports. A compound is "attached" to a solid support when it is associated with the solid support through a non-random chemical or physical interaction. In some preferred embodiments, the attachment is through a covalent bond.

As used herein, the terms "linker" and "linker group" are used interchangeably to refer to chemical moieties that are attachable to a solid support on one end and an anchor group or polymer on the other end. The "linker" and "linker group" are atoms or molecules that link or bond two entities (e.g., solid supports, oligonucleotides, or other molecules), but that is not a part of either of the individual linked entities. In general, linker molecules are oligomeric chain moieties containing 1-200 linearly connected chemical bonds. One end of a linker chain is immobilized on substrate surface, such as through —SiO— bond formation. The other end of a linker chain contains a functional group that can be converted to an OH or an $NH_2$ group. Examples of linkers include, but are not limited to the chemical moieties shown in FIG. 1 and —$(OCH_2CH_2)_n$—, wherein n is from about 1 to about 20. The use of a variety of alkyl amide groups is contemplated, including —$(CH_2)_m$—C(O)NH—$(CH_2)_n$— and —$(OCH_2CH_2)_m$—C(O)NH—$(OCH_2CH_2)_n$—, wherein m and n can be the same or different and m and n are from about 1 to about 20. The use of a variety of amide groups having the linking units of alkyl or ether bonds is contemplated, including —$R_1$—C(O)NH—$R_2$—, wherein $R_1$ and $R_2$ are alkyl, ether, and polyether groups. Linkers can have substitutions to have branched chain structures, such as dendritic structures. Multiple linkers can be covalently connected to form an extended linker chain.

The term "anchor group or moiety" refers to a chemical moiety that connects a linker and a synthesized oligonucleotide or other polymer and which can be selectively cleaved to release oligonucleotides or other polymers from substrate surface. For example, the anchor may include the structure —C(X)—C(Y)— (X may be $OPO_2O$-oligonucleotide), (Y is a functional group that may function as a nucleophile, for example, Y may be an OH, $NH_2$ or SH). Preferably, the —C(X)—C(Y)— is part of a ring moiety and further a five member ring moiety. The anchor may include dU, abasic group, ribonucleotides, thioate phosphodiester, when incorporated into oligonucleotides, which can selectively cleaved by treatment with specific enzymatic digestion or chemical degradation conditions.

The term "protected nucleotides" refers to nucleotides containing nucleobase protecting groups, such as 4-NH-benzol in cytidine and adenine and 2-NH-isobutyryl in guanosine, sugar protecting groups, such as 2'-O-t-butyldimethylsilyl in ribonucleotides, and phosphate protecting groups, such as P—O-(2-cyano)ethylphosphine, etc. "Protecting group" refers to a molecule or chemical group that is covalently attached to a moiety of a compound to prevent chemical modification of the moiety of the compound or modification of specific chemical groups of the compound. For example, protecting groups may be attached to a reactive group of a compound to prevent the reactive group from participating in chemical reactions including, for example, intramolecular reactions. In some cases, a protecting group may act as a leaving group, such that when the molecule is added to another compound in a desired synthesis reaction, the protecting group is lost, allowing a reactive group to participate in covalent bonding to the compound. The phosphoramidites of the present invention typically contain one or more protective groups prior to their addition to nucleic acid molecules. For example, the reactive phosphate of the phosphoramidite (i.e., the phosphate group that is covalently attached to another molecule when the phosphoramidite is added to the other molecule) may contain one or more protecting groups. A detailed description of phosphoramidites and their addition to nucleic acid molecules is provided Beaucage and Iyer (Tetrahedron 49:1925 [1993]), herein incorporated by reference in its entirety.

As used herein, the term "stable", when used in reference to a linker or an anchor group, refers to a property of the compound or the chemical moiety which is not cleaved by certain reactions conditions, but selectively cleavable by different reaction conditions. These orthogonal reactions are well established in solid phase synthesis. The present invention is not limited to any particular set of selective cleavage conditions. Indeed, the present invention contemplates that the siloxane linkers are stable under anhydrous ethylene diamine treatment, but a variety of cleavage conditions may be utilized when appropriate, including base hydrolysis of the Si—O bond. Further, the present invention contemplates that the 1,2-diol anchors are stable to basic hydrolysis when one of the OH group is protected with a protecting moiety, but a variety of cleavage conditions may be utilized after the OH protecting group is removed, including 2-OH assisted 1-phosphate hydrolysis under basic conditions. Thus, the present invention contemplates in one embodiment linkers and/or anchor groups that are stable to basic hydrolysis. In another embodiment, the present invention contemplates linkers and/or anchor groups that are stable to acid hydrolysis.

As used herein, the term "selective cleavable", when used in reference to a linker or an anchor group, refers to a property of the compound or the chemical moiety is not cleaved by certain reactions conditions, but selectively cleavable by different reaction conditions. These orthogonal reactions are well established in solid phase synthesis. The present invention is not limited to any particular set of selective cleavage conditions. Indeed, the present invention contemplates that the siloxane linkers are stable under anhydrous ethylene diamine treatment, but a variety of cleavage conditions may be utilized when appropriate, including base hydrolysis of the Si—O bond. Further, the present invention contemplates that the 1,2-diol anchors are stable to basic hydrolysis when one of the OH group is protected with a protecting moiety, but a variety of cleavage conditions may be utilized after the OH protecting group is removed, including 2-OH assisted 1-phosphate hydrolysis under basic conditions. Further, the present invention contemplates that dU, abasic moiety, ribonucleotides, and thioate phosphodiester are stable under regular DNA or RNA synthesis conditions but may be selectively cleaved by specific chemical or enzymatic treatments.

As used herein, the term "substrate attaching group" refers to any chemical group that is useful for attaching a linker to a substrate. Examples of substrate attaching groups include, but are not limited to, monochlorosilyl, monoalkoxysilyl, trichlorosilyl or trialkoxysilyl groups.

As used herein, the term "polymer attaching group" refers to a functional group or groups that can be converted to a functional group, for example, an OH or an $NH_2$ group, that is used for initiating synthesis of a polymer on a linker or attaching an anchor moiety to a linker. Examples of polymer attaching groups include, but are not limited to, amino, hydroxy, thiol, carboxylic acid, ester, amide, isocyanate or isothiocyanate group, most preferably an OH or a $NH_2$ group. Methods for such functionalization are well known in the art (See, e.g., Bigley et al., J. Chem. Soc. (B):1811-18 (1970).

As used herein, the term "synthesis initiation site" refers to a chemical group on a linker or an anchor moiety or any other chemical entity that is used as a site for initiating synthesis of a polymer chain.

As used herein, the term "spacer" refers to a chemical group connected to a linker or an anchor moiety that is used to extend the length of the linker moiety and as a site for initiating synthesis of a polymer chain. Examples of spacer include, but are not limited to, ethyleneglycol polymer, alkyl, oligonucleotides, peptides, peptditomimetics.

The term "oligonucleotide" as used herein is defined as a molecule comprising two or more deoxyribonucleotides or ribonucleotides, preferably at least 4 nucleotides, more preferably at least about 10-15 nucleotides and more preferably at least about 15 to 200 nucleotides. The exact size will depend on many factors, which in turn depend on the ultimate function or use of the oligonucleotide. The oligonucleotide may be generated in any manner, including chemical synthesis, DNA replication, reverse transcription, PCR, ligation, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. An oligonucleotide sequence is written in 5'- to 3' direction by convention.

As used herein, the term "co-coupling agent" refers to a compound which when incorporated into a polymer serves as chain terminator, i.e. terminating the chain growth. The co-coupling agent preferably has a structure similar to the monomers used in the polymer synthesis reaction. The co-coupling agent can be mixed with coupling agent in the synthesis, resulting in a mixture of extendible and non-extendible sequences that no longer can be extended and sequences that can continuously grow in length.

As used here in the term "coupling agent or monomer" refers to a building block in polymer synthesis. The compound has a reactive group which reacts with functional groups of the reacting compounds on solid surface and has a protected reactive group which in a later synthesis step can be deprotected to form reactive functional group for further reaction with another coupling agent or monomer.

As used here in the term "terminator or chain terminator" refers to a compound which does not contain the same protected reactive sites as the coupling agent. Therefore, when included in an appropriate ratio with a coupling agent or monomer, terminator forms a number of inactive sequences that cannot be extended in further reactions. Examples of terminator or chain terminator useful in the present invention include nucleophosphoramidites and nucleophosphonates that cannot be extended, for example 5'-MeO-T.

As used herein, the terms "complementary" or "complementarity" are used in reference to oligonucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of oligonucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity of at least two compounds or sequences. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the thermodynamics of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences and sufficient hybridization stability. Thus, conditions of "weak" or "low" stringency are often required when it is desired that nucleic acids which are not completely complementary to one another or have lower hybridization stability be hybridized or annealed together.

The term "label" as used herein refers to any atom or molecule that can be used to provide a detectable (preferably quantifiable) signal, and that can be attached to a nucleic acid or protein or other polymers. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the term "dye" refers to a molecule, compound, or substance that can provide an optically detectable signal (e.g., fluorescent, luminescent, colorimetric, etc). For example, dyes include fluorescent molecules that can be associated with nucleic acid molecules (e.g., Cy3).

As used herein, the term "directly bonded," in reference to two or more molecules refers to covalent bonding between them without any intervening linking group or spacer groups that are not part of parent molecules.

As used herein, the term "purified" or "to purify" refers to the removal of contaminants, such as metal ions, from a sample of the desired synthesized polymer. In like manner, the terms "purified" or "to purify" may also refers to enrichment of the desired synthesized polymer relative to other components in a sample. For example, the present invention contemplates purification wherein the desired synthesized polymer is present in amounts that represent 50% or greater of the components in a sample (and more preferably, 70% or greater; still more preferably 80% or greater; and most preferably greater than 90%). Removal of contaminants or enrichment of the desired synthesized polymer can refer to samples that have the desired polymer attached to a support or samples in which the desired polymer has been cleaved from the support. In one embodiment, the present invention contemplates purification wherein greater than 90% of contaminants have been removed.

DESCRIPTION OF THE INVENTION

A variety of synthetic approaches have been developed for preparation of oligonucleotide sequences. Typically, oligonucleotides are synthesized utilizing a building block approach which involves the sequential addition of nucleotides onto a growing oligonucleotide chain immobilized on to a solid support. Because every DNA oligonucleotide may have any of 4 different initial nucleotides, it is necessary to maintain a supply of 4 different nucleoside (A, C, G and T) loaded solid supports to be able to synthesize any given DNA sequence. In the case of DNA synthesis, the first nucleoside from the 3' end of the DNA sequence is typically preloaded on the solid support through an ester linkage. For example, if the sequence that is to be synthesized contains a T nucleoside at the 3' end, a T support is employed and the balance of the nucleotides in the DNA sequence added thereto (e.g., using an automated DNA synthesizer). At the end of the total DNA synthesis, the oligonucleotide is cleaved from the solid support through the hydrolysis of the ester linkage. Taking into consideration RNA synthesis procedures, an additional 4-different nucleoside loaded solid supports must be available to the user. Similar considerations apply if any specialty modified nucleoside is desired at the 3' end.

Maintaining a supply of at least 8 different prederivatized solid supports is inconvenient and expensive. An additional consideration is the relatively short shelf life of nucleoside derivatized solid supports. Typically, after one year storage such solid supports are not longer usable. There is also the possibility that synthetic procedures may be initiated mistakenly with the wrong support leading to disastrous consequences in the final applications of the oligonucleotides.

In order to alleviate these problems some researchers have pursued developing some type of universal solid support. For example, deBear et al. derivatized glass supports with 2'(3')-O-benzoyluridine 5'-O-succinyl so that the uridine moiety is linked to the glass via an ester (succinate) linkage. [de Bear et al., Nucleosides and Nucleotides 6, 821-830 (1987)]. Oligonucleotide synthesis takes place by adding nucleotide monomers to the 2' or 3' position of the uridine. Following the synthesis, the new oligonucleotides can be released from the glass, deprotected and cleaved from the uridylyl terminus in one reaction. The uridyl functionality is cleaved from the solid support in this cleaving reaction.

Crea and Horn suggested a similar approach which involved preparing the dimer 5'-O-p-chlorophenylphospho-2'(3')-O-acetyluridilyl-[2'(3')-3']-5'-O-dimethoxytritylthymidine p-chlorophenylester and attaching the dimer to cellulose via a phosphate linkage. [R. Crea & T. Horn, Nucleic Acids Research 8, 2331 (1980)]. The 5' position of the thymidine is available for oligonucleotide attachment and synthesis. The subsequent use of aqueous concentrated ammonia results in the release of the synthesized oligonucleotide from the cellulose leaving the uridine portion of the dimer attached to the cellulose. Although Crea and Horn utilized the reactive vicinal OH groups on the uridine as the release site for the oligonucleotide from the uridine, the solid support suggested in this reference is not a universal solid support since the initial oligonucleotide is incorporated in the solid support reagent and a different support is required for oligonucleotides incorporating a different first nucleoside.

More recently, Schwartz et al. attached an adapter, 2'(3')-O-dimethoxytrityl-3'(2')-O-benzoyluridine-5'-O-2-cyanoethyl N,N-diisopropylphosphoramidite, to a thymidine derivatized polystyrene and synthesized an oligonucleotide from the O-dimethoxytrityl (O-DMT) position of the uridine after removal of the DMT group (M. E. Schwartz, R. R. Breaker, G. T. Asteriadis, and G. R. Gough, Tetrahedron Letters, Vol. 36, No. 1, pp 27-30, 1995). While this approach provides a universal solid support for oligonucleotide synthesis, the cleaving step releases the adapter and the thymidine from the support and then cleaves the synthesized oligonucleotide from the uridine. Thus, the purification process requires removing the thymidine linker and the cleaving processes.

The aforementioned solid supports and methods for their use have several disadvantages in terms of the convenience and efficiency of the subsequent oligonucleotide cleaving steps. When ammonia which has been widely accepted as a safe reagent for DNA synthesis is utilized for cleaving, as taught by deBear et al., the cleavage time is as long as 24 hours at 65° C. In view of the growing trend to produce oligonucleotides as quickly as possible, this is an unacceptably long period of time. Decreasing the time required for cleaving the uridylyl from an oligonucleotide at the uridine 3' position typically uses $Pb^{2+}$ or $Mg^{2+}$ ion catalyst system or the action of strong alkali hydroxides. Necessarily these processes require a separate isolation step to remove the ion used. Additionally, when strong alkali bases are used in the cleaving processes, considerable side reactions in the form of cytosine deamination occur.

U.S. Pat. No. 5,919,523 (Affymetrix; incorporated herein by reference) describes derivatization of solid supports and methods for oligomer synthesis. The methods provide polymer-coated support for use in solid-phase synthesis (polyethyleneimine, polyethyleneglycol, polyvinyl alcohol, etc.). The polymer coating may be functionalized to contain synthesis initiation sites. The method also describes reducing surface density of functional groups using protected amino acids to react with functional groups on polymer coating.

PCT publication WO046231 (Amersham; incorporated herein by reference) describes a method for purifying an oligonucleotide that comprises providing an oligonucleotide attached to a substrate, wherein the oligonucleotide contains phosphate protecting groups; contacting the oligonucleotide with a reagent, e.g., an organic amine, that cleaves the phosphate protecting groups from the oligonucleotide without detaching the oligonucleotide from the substrate; isolating the oligonucleotide attached to the substrate from the cleaved phosphate protecting groups; and cleaving the oligonucleotide from the substrate. The side reactions involving acrylonitrile (formed from deprotection of phosphate) and nucleotides can be avoided. This method provides crude oligonucleotide mixtures that are easier to purify and from which the desired full-length oligonucleotide product. Linkers used are those on standard CPG containing a succinyl linkage.

U.S. Pat. No. 5,738,829 (T. Kempe; incorporated herein by reference) describes an apparatus connected to a DNA synthesizer for gas phase deprotection of oligonucleotides that are covalently bound to solid support using ammonia or ammonium hydroxide vapors.

U.S. Pat. No. 5,656,741 (Chow, F. and Kempe, T., incorporated herein by reference) describe a process for the cleavage, deprotection, and recovery of a synthetic oligonucleotide by immersing the support in a basic solution, whereby cleavage occurred first and followed by deprotection. The cleaved and deprotected oligonucleotide was recovered by precipitation from solution.

U.S. Pat. No. 5,750,672 (Kempe, T., incorporated herein by reference) describes a method for recovering synthesized oligonucleotides from a solid support that includes the step of incubating the solid support with an anhydrous amine reagent under conditions suitable to cleave and deprotect the oligonucleotide. The cleaved and deprotected oligonucleotide will be substantially insoluble in the reagent and/or will exhibit preferential affinity for the support. Reagent kits for use in such a method and cleaved, deprotected oligonucleotides prepared by means of such a method are provided.

U.S. Pat. No. 5,869,696 (Beckman Instruments; incorporated herein by reference) describes universal solid support oligonucleotide synthesis reagents, oligonucleotide synthesis processes, and reagents for cleaving oligonucleotides from solid supports. Oligonucleotide synthesis on solid support is through a ring moiety having vicinal groups that can attack the other when one of the two is not protected, causing cleavage of oligonucleotide synthesized. The linkage between the ring moiety and the support is not stable to the cleavage condition. The universal support is intended to reduce the number of the types of support needed for conventional oligonucleotide synthesis on cleavable linkers.

U.S. Pat. No. 6,090,934 (Kumar, P. and Gupta, K. C., incorporated herein by reference) describes a universal polymer support containing an organic aliphatic molecule of structure having a least a pair of cis-hydroxyl groups where on of the hydroxyl groups is attached to the polymer support through a covalent linkage and the other hydroxyl group is protected by an acid labile group, which is activated for oligonucleotide synthesis. Upon completion of the synthesis, the oligonucleotide on solid support is treated with a basic solution. The cleavage of the linkage between the aliphatic molecule and the polymer support frees a hydroxyl, which in turn attacks the adjacent phosphate group to form cyclic phosphate and give free oligonucleotide.

U.S. Pat. No. 6,015,895 (Pon, R. T. and Yu, S, incorporated herein by reference) describes a process for producing a chemically modified solid support for oligonucleotide synthesis, the process comprising the steps of reacting a linker compound, which is a substituted or unsubstituted C1-C20 alkyl group, a substituted or unsubstituted C5-C30 aryl group and a substituted or unsubstituted C5-C40 alkaryl group, with an OH of a desired nucleoside to produce a derivatized nucleoside having an ester linkage; and a solid support capable of entering into an esterification reaction, to produce the linker arm.

U.S. Pat. No. 6,043,353 (Pon, R. T. and Yu, S, incorporated herein by reference) describes reusable solid support having linkers consisting of a substituted or unsubstituted C1-C20 alkyl group, C5-C30 aryl group, or C5-C40 alkylaryl group. The linker groups have a stable portion linked to another portion through a base cleavable bond, such as an ester bond. The stable portion of the linker can be reused after each cleavage of oligonucleotides from support.

The present invention provides improved systems for synthesizing polymers on solid supports. In particular, the present invention provides linker systems that provide an increased density of reaction sites on solid supports. In one embodiment, the present invention achieves a density such that the linkers are at least two times (and more preferably at least four times) more densely packed (e.g., on a surface) than conventional linkers. These linker systems improve stability of linkers and the linker-polymer connectivity under normal polymer reaction conditions, such as in amine solutions. The present invention is not limited to any particular mechanism. Indeed, an understanding of the mechanism is not required to practice the present invention. Nevertheless, it is believed that the increased packing density of the linker systems of the present invention provide both a more ordered surface and increased resistance to cleavage as compared to conventional linker systems. In preferred embodiments, the stable linkers are modified to include a cleavable anchor group at the end of the linker opposite of the solid support. The polymer (e.g., polynucleotide or polyamino acid) is then synthesized from a starting point (e.g., a functional group) on the anchor molecule. Following synthesis of the polymer, the protecting groups on the polymer can be removed, the solid support can be conveniently washed and then treated under appropriate conditions so that the anchor group is cleaved, releasing the washed polymer from the support. The density of the polymers synthesized on the solid support can be conveniently controlled by including co-coupling agents that are structurally similar to the monomers of the polymer being synthesized. The co-coupling agents terminate polymer synthesis at sites where they incorporated, thereby decreasing the number of polymer chains synthesized. The polymer synthesized can be applied to various applications. Reagents and methods provided by the present invention are described below in the following sections:

I. Solid Supports

It is contemplated that the reagents and methods of the present invention may be utilized with a variety of solid supports. In general, any solid support that may be derivatized with the linker groups (See Section II) of the present invention finds use in the present invention. Accordingly, the present invention is not limited to the use of any one solid support.

In particular, the solid substrate may be biological, nonbiological, organic, inorganic, or a combination of any of these, existing as particles, strands, precipitates, gels, sheets, tubing, spheres, containers, capillaries, pads, slices, films, plates, slides, etc. The solid substrate is preferably flat but may take on alternative surface configurations. For example, the solid substrate may contain raised or depressed regions on which synthesis takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, nitrocellulose and nylon membranes, or any one of a variety of gels or polymers such as (poly)tetrafluoroethylene, (poly)vinylidendifluoride, polystyrene, polycarbonate, or combinations thereof. Other suitable solid substrate materials will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as those found on silica surfaces.

II. Linker Groups

A linker group typically has two ends, wherein one of the ends comprises a substrate attaching group and wherein the other of the ends comprises a polymer attaching group, wherein the polymer attaching group is preferably covalently linked to an anchor moiety and the anchor group has an attaching group for polymer synthesis. The present invention is not limited to any particular linker group. Indeed, the use of a variety of linker groups is contemplated, including, but not limited to, alkyl, ether, polyether, alkyl amide groups or a combination of these groups. The present invention is not limited to the use of any particular alkyl group. Indeed, the use of a variety of alkyl groups is contemplated, including —$(CH_2)_n$—, wherein n is from about 4 to about 20. The use of a variety of ether and polyether groups is contemplated, including —$(OCH_2CH_2)_n$—, wherein n is from about 1 to about 20. The use of a variety of alkyl amide groups is contemplated, including —$(CH_2)_m$—C(O)NH—$(CH_2)_n$— and —$(OCH_2CH_2)_m$—C(O)NH—$(OCH_2CH_2)_n$—, wherein m and n can be the same or different and m and n are from about 1 to about 20. The use of a variety of amide groups having the linking units of alkyl or ether bonds is contemplated, including —$R_1$—C(O)NH—$R_2$—, wherein $R_1$ and $R_2$ are alkyl, ether, and polyether groups. The linkers can be terminated with a functional group, such as OH, SH, NHR (R=H or substitution group, such as $CH_3$, $CH_2CH_3$, Ph), aldehyde, carboxalic acid, ester, or other typical reactive groups. The linkers can also connect to an anchor group or a polymer. Multiple linkers can be covalently connected to form an extended linker chain.

The present invention is not limited to the use of any particular substrate attaching group. Indeed, the use of a variety of substrate attaching groups is contemplated, including, but not limited to chlorosilyl, alkyloxysilyl, alkylchlorosily, and alkylalkoxysily functional groups. The present invention is not limited to the use of any particular polymer attaching group. Indeed, the use of a variety of polymer attaching groups is contemplated, including, but not limited to amine, hydroxyl, thiol, carboxylic acid, ester, amide, epoxide, isocyanate, and isothiocyanate groups.

In preferred embodiments, a silicon-containing substrate is functionalized with a hot pirhana solution (e.g., concentrated $H_2SO_4$:$H_2O_2$, 50:50 v/v) for a short period of time (e.g., 15 min). The —$(CH_2)_6CHCH_2$ linker that includes a silane functionality as part of its substrate attaching group is then reacted with the functionalized substrate to provide a substrate or solid support derivatized with a linker group. The polymer attaching group is then functionalized by treatment with a suitable functionalizing agent (e.g., $BH_3$/THF/$H_2O_2$, $BH_3$/NaOAc, $BH_3$/NaOH, or $BH_3$/NaOH).

The present invention is not limited to any particular mechanism. Indeed, an understanding of the mechanism is not required to make and the invention. Nevertheless, the use of the linkers described above provides a derivatized surface comprising a higher density of the linking groups. It is contemplated that the high density of linking groups results in higher yield of the total sequences synthesized on solid surfaces and may increase the resistance to surface cleavage during normal polymer synthesis steps such as activation and deprotection of phosphoramidites. It is contemplated that the increased sequence density due to different linkers used is highly desirable for the subsequent applications of the polymers, such as oligonucleotides and peptides. The resistance to cleavage will allow the multiple usage of biochips, thereby greatly reducing the costs associated with such chips.

The increased density of the linking groups of the present invention can be assayed by loading of controlled porous glass (CPG). In preferred embodiments, the linking groups of the present invention are capable of a loading density on CPG (>500 Å pore size) of about greater than 10 μmol/g of CPG, preferably greater than 20 μmol/g of CPG, and most preferably greater than about 100 μmol/g of CPG.

III. Anchor Groups

The present invention also provides anchors groups or moieties for attachment to the linker through the polymer attachment group. In preferred embodiments, the anchor group includes a reactive site for attachment to the polymer attachment site of the linker. In further preferred embodiments, the anchor group includes a synthesis initiation site from which a polymer can be synthesized. In still further preferred embodiments, the anchor is selectively cleavable, preferably not being cleaved by regular synthesis, including coupling and deprotecting steps.

In particular, in some embodiments, the anchor groups of the present invention are organic aliphatic molecules (e.g., butane-2,3-diol, 1,2,3-trihydroxyheptane, 1,2,3-hexanetriol and the like) of the following general structure:

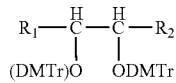

where $R_1$=H—$(CH_2)_n$— and $R_2$=—$CH_2$—OH, —$(CH_2)_n$—H; n=1-4; and DMTr=4,4'-dimethoxytrityl. Those skilled in the art will recognize that other protecting groups may be utilized in place of DMT.

The present invention is not limited to the use of any particular anchor moiety. Indeed, the use of a variety of anchor moieties is contemplated, including, but not limited to, those of the following 1,2-diol derivatives of structures shown below:

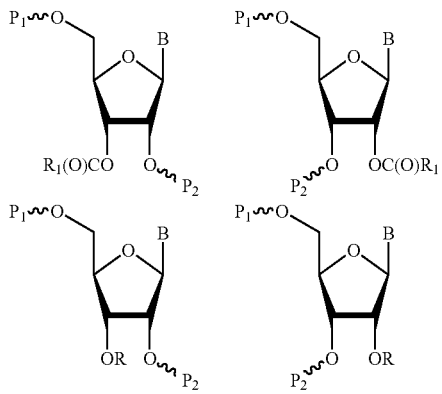

Wherein $P_1$ and $P_2$ are chain units comprised of linker and polymer or polymer; B is a nucleobase; $R_1$ are substitution groups, such as $CH_3$, $R_2Ph$ ($R_2$ are substitution groups on the phenyl ring, such as $SCH_3$, Cl, $NO_2$), $CH_2CH_2CN$. R is a protecting group, which is $OC(O)R_1$, t-butyldimethylsilyl (TBDMS), or other protecting groups used for 2'- or 3'-O protection of ribonucleotides. Once the protecting group is removed, the adjacent OH can accelerate the hydrolysis of the phosphordiester bond, resulting in cleavage of the polymer chain.

The diol compounds can be treated with one equivalent of a homobifunctional alkanoic acid halide (e.g., oxalyl chloride, succinoyl chloride, adipoyl chloride and the like) and reacted with the polymer attachment group which has hydroxyl or aminoalkyl functionalities. The unreacted functional groups in the above diol derivatives then can then be capped with dry alkanol (e.g., MeOH, EtOH, propanol and the like) for blocking the residual functional groups followed by washing with dry alkanol and dialkyl ether, respectively.

In other embodiments of the present invention, the anchor molecule has the following general structure:

Rs-L-Rp wherein L is a linker group (which may in turn be covalently bound to a solid substrate as described above); $R_s$ is the surface attaching group; $R_p$ is the polymer attaching group and it is

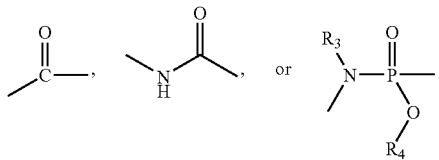

or an ether containing group (e.g., polyethylene glycol), where $R_3$ is hydrogen or alkyl and $R_4$ is a phosphate protecting group; and $R_b$ is a ring moiety having vicinal groups —$XR_1$ and —$YR_2$ wherein each of X and Y is independently selected from the group consisting of O, S and NH and one of $R_1$ and $R_2$ is a blocking moiety and the other is hydrogen or a hydroxy protecting group suitable for protecting OH, SH, or $NH_2$. Recognizing that when $R_p$ is a phosphoramidite or its oxidized form phosphoramidate, those skilled in the art will appreciate that $R_3$ is preferably hydrogen. This is because these oligonucleotide synthesis reagents are generally prepared using a primary amine. However, those skilled in the art will also appreciate that $R_3$ can be alkyl because the phosphoramidate can be prepared using secondary amines. Phosphate protecting group $R_4$ is suitably any group capable of protecting the phosphorous of the phosphoramidate or phosphoramidite from cleaving or reacting during oligonucleotide synthesis. Those skilled in the art will recognize that cyanoethyl moieties are preferred phosphate protecting groups for their stability under oligonucleotide synthesis conditions and their ease of removal with ammonia or methylamine. However, it will be understood that because the phosphoramidate or phosphoramidite linkage of the type utilized in the present invention need not be deprotected and thus alkyl moieties generally or aryl containing moieties are also suitable phosphate protecting groups $R_4$.

It is contemplated that vicinal groups —$XR_1$ and —$YR_2$ are most effective when they are positioned cis with respect to each other ($R_1$ and $R_2$ are H or substitution groups). Since adjacent functionalities attached to ring moieties can be present in a cis configuration, and preferably a ring moiety and —$XR_1$ and —$YR_2$ are oriented in space in a fixed cis position. However, —$XR_1$ and —$YR_2$ can be from straight chained moieties having suitable vicinal constituents, such as glycerol.

Those skilled in the art will appreciate that because of their availability on sugars and glycerol type diols, and because of known protecting groups suitable for their protection, X and Y are preferably O (oxygen). However, it will be apparent to those skilled in the art that utilizing NH and S in such positions for the purposes of the present invention is within the scope of the present invention.

In order to block one of the vicinal positions from participating in the oligonucleotide synthesis, $R_1$ or $R_2$ of vicinal $OR_1$ and $OR_2$ are suitable blocking groups. Because, as described below, the unblocked oxygen is active in the final oligonucleotide cleaving step, the blocking group should be easily removed under cleaving reaction conditions but stable under those conditions typically found in oligonucleotide synthesis. For this reason one of $R_1$ or $R_2$ is preferably an alkylcarbonyl or arylcarbonyl, such as acetyl or benzoyl. An alkylcarbonyl moiety is an aliphatic group terminating in C=O, wherein the aliphatic component comprises one (i.e., Acetyl) to about 10 carbon atoms. By an arylcarbonyl group is meant a residue comprising at least one homoaromatic or heteroaromatic ring and terminating in C=O (e.g., $C_6H_5CO$). The protecting groups $R_1$ or $R_2$, which are not a blocking group, are suitably any protecting groups which are easily removed so that the protected group is available as the site for the introduction of a first nucleoside during the initiation of oligonucleotide synthesis. For purposes of the present invention, the 4,4'-dimethoxytrityl (DMT) group is particularly preferred. Other suitable groups include, but are not limited to, the following: 4,4',4"-tris-(benzyloxy)trityl (TBTr); 4,4',4"-tris-(4,5-dichlorophthalimido)trityl (CPTr); 4,4',4"-tris(levulinyloxy)trityl (TLTr); 3-(imidazolylmethyl)-4,4'-dimethoxytrityl (IDTr); pixyl (9-phenylxanthen-9-yl); 9-(p-methoxyphenyl)xanthen-9-yl (Mox); 4-decyloxytrityl ($C_{10}$ Tr); 4-hexadecyloxytrityl ($C_{16}$ Tr); 9-(4-octadecyloxyphenyl)xanthene-9-yl ($C_{18}$ Px); 1,1-bis-(4-methoxyphenyl)-1'-pyrenyl methyl (BMPM); p-phenylazophenyloxycarbonyl (PAPoc); 9-fluorenylmethoxycarbonyl (Fmoc); 2,4-dinitrophenylethoxycarb only (DNPEoc); 4-(methylthiomethoxy)butyryl (MTMB); 2-(methylthiomethoxymethyl)-benzoyl (MTMT); 2-(isopropylthiomethoxymethyl)benzoyl (PTMT); 2-(2,4-dinitrobenzenesulphenyloxymethyl)benzoyl (DNBSB); and levulinyl groups. These and other suitable protecting groups are described in detail in Beaucage, S. L. and Iyer, R. P. Tetrahedron 48, 2223-2311 (1992), the entire disclosure of which is hereby incorporated by reference.

In particularly preferred embodiments of the present invention, the anchor monomer has the following structure:

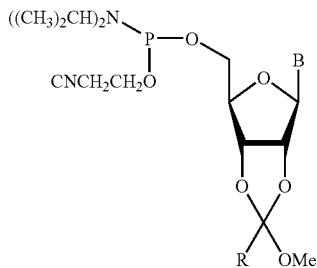

Wherein R is H or $CH_3$. For purposes of the present invention, B represents a pyrimidine or purine base. Preferred for use in accordance with the present invention are those bases characteristic of guanine, adenine, thymine and cytosine; however, other purine or pyrimidine bases as may be employed in the synthesis of nucleotide analogs may alternatively be used as group B.

IV. Polymer Synthesis

The solid substrate-linker-anchor moiety or solid substrate-linker compounds described above serve as useful universal supports for the synthesis of polymers (e.g., polynucleotides and polyamino acids). In general, the polymers may be synthesized by any means known in the art, including phosphoramidite mediated synthesis, photolithography (see, e.g., U.S. Pat. Nos. 5,424,186 and 5,744,305, each of which is incorporated herein by reference) or photogenerated acid mediated synthesis in combination with selective irradiation by a spatial optical modulator (See, e.g., WO 99/41007, incorporated herein by reference). Materials and protocols for phosphoramidite mediated synthesis of oligonucleotides are well known in the art and available from Glen Research, Sterling Va. Phosphite triester and H-phosphonate chemistries are commonly used to prepare oligonucleotides on a solid support or substrate. Large scale commercial DNA synthesizers that employ phosphite triester chemistry, have made the production of multi-kilo grams of oligonucleotides possible.

Nucleosides used in large scale synthesis of oligonucleotides on a solid phase by phosphoramidite chemistry use are protected with suitable groups that prevent formation of side products during oligonucleotides synthesis. The reactive exocyclic amine groups found on the nucleobases in monomer building blocks are generally protected with benzoyl, isobutyrl, phenoxyacetyl, and acetyl protecting groups, while the phosphate groups are usually protected as 2-cyanoethyl phosphoramidites. Such protective groups are easily removed after completion of the oligonucleotide synthesis by treatment with a concentrated solution of ammonium hydroxide.

The oligonucleotide is assembled by sequential addition of 5'-dimethoxytritylated-3'-nucleoside phosphoramidites to the unmasked 5'-hydroxy group of the first nucleoside loaded on to the support. This addition is catalyzed by a mildly acidic catalyst such as tetrazole or dicyanoimidazole. The corresponding phosphite triester internucleotide linkage is then converted to a more stable phosphate triester by oxidation with iodine or peroxides. "Capping" of any unreacted 5'-hydroxyl groups by converting them to corresponding esters is achieved by a brief exposure to capping reagents containing acetic anhydride. Next, removal of 5'dimethoxytrityl group from the newly added nucleoside under mildly acidic conditions generates the 5'-hydroxyl group and completes the coupling cycle. Using this method, a coupling efficiency of greater than 99% in each coupling step can be achieved. Towards the end of oligonucleotide synthesis, the dimethoxytrityl group of the terminal nucleotide at the 5'-end is either left intact ("trityl-on") or cleaved to give an oligonucleotide with free 5'-terminal hydroxyl group ("trityl-off"). The 5'-trityl group may be used as a lipophilic purification handle to purify the full-length oligonucleotide bearing the trityl group from shorter and non-tritylated species by reverse HPLC. After completion of oligonucleotide synthesis, the succinic ester linkage is cleaved under alkaline conditions to release the oligonucleotide from the substrate in addition to the removal of protective groups from the nucleobases and the phosphate backbone. This process usually takes about 24 hours at room temperature or about 6 hours at 55° C.

Several different methods for creating arrays of sequences on solid supports (e.g., gene chips) are also known in the art. The universal supports described above are useful as supports for array synthesis. In some embodiments, the array synthesis is by photolithography methods (See, e.g., U.S. Pat. No. 5,143,854, incorporated herein by reference). In other embodiments, the array synthesis is performed by a maskless procedure, such as those described in WO 99/41007 and WO 99/42813, each of which is incorporated herein by reference. Each of these methods employ the light mediated deprotection or activation of reactive sites on the growing polymer chains in discrete, predefined regions.

The principles of solid phase chemical synthesis of polypeptides are well known in the art and may be found in general texts in the area such as Dugas, H. and Penney, C., Bioorganic Chemistry (1981) Springer-Verlag, New York, pgs. 54-92, Merrifield, J. M., Chem. Soc., 85:2149 (1962), and Stewart and Young, Solid Phase Peptide Synthesis, pp. 24-66, Freeman (San Francisco, 1969). For example, polypeptides of the present invention may be synthesized by solid-phase methodology utilizing an Applied Biosystems 430A peptide synthesizer (Applied Biosystems, Inc., 850 Lincoln Center Drive, Foster City, Calif. 94404) and synthesis cycles supplied by Applied Biosystems. Boc amino acids and other reagents are commercially available from Applied Biosystems and other chemical supply houses.

Accordingly, in some preferred embodiments, the present invention provides methods for synthesizing polymers, nucleic acids, peptides, carbohydrates, lipids, PNAs, on universal supports that comprise densely packed linker groups that form a more ordered layer than previously described substrates. It is contemplated that the densely packed linkers are resistant to cleavage and increase the capacity of the solid support. Therefore, in some embodiments, the present invention provides methods for synthesizing polymers comprising providing a substrate, stable linkers, an anchor group, and monomers, derivatizing the substrate with the stable linkers, attaching the anchor group to the linkers to form a substrate-linker group-anchor group moiety, and synthesizing a polymer from the monomers on the substrate-linker group-anchor group moiety. In preferred embodiments, the monomers are protected monomers and synthesis proceeds deprotecting the protected monomers under conditions which do not cleave the polymer from the substrate, adding the desired protected monomer, and repeating until the desired polymer is synthesized.

In still further preferred embodiments, the present invention provides methods for controlling the number of polymers synthesized in a designated area. In these embodiments, a co-coupling agent that is a chain terminator that is similar in structure to the monomers is used in the synthesis reaction. When included in an appropriate ration, the co-coupling reagent forms a number of inactive sequences within the given region that cannot be extended. Examples of co-coupling agents useful in the present invention include nucleophosphoramidites and nucleophosphonates that cannot be extended, for example 5'-MeO-T (See FIG. 2).

V. Polymer Deprotection, Washing, and Release

The present invention also provides improved methods for deprotecting, washing, and releasing polymers synthesized on the derivatized substrate. In particular, as described above, the anchor moiety is selectively cleavable. As the growing polymer chain is continually deprotected under basic conditions, such as EDA in anhydrous EtOH, the polymer attached to the substrate is not cleaved from the substrate. Upon completion of the deprotection reactions, the substrate surface is rinsed to remove small molecular fragments resulting from the deprotection. This provides a surface with the polymer attached that is free of salt and other small molecular contaminants. The polymers are then removed from the substrate through a neighboring group assisted reaction, for example, 2-OH assisted 1-phosphate hydrolysis. Preferably the cleavage agent is volatile (e.g., it can be removed via freeze drying) and non-ionic. The cleaved oligonucleotides are then recovered by rinsing the substrate surface and the solution evaporated. When the polymer is a oligonucleotide, the oligonucleotide are suitable for use as primers, templates, diagnostic probes, mass analysis and other applications, such as any enzymatic process, including DNA replication, reverse transcription, primer extension, phosphorylation, ligation, phosphorylation, cleavage by restriction enzymes, etc., as naturally occurring oligonucleotide sequences. Previously described cleavage steps relied on the use of solvents containing metal ions such as $Mg^{2+}$ or $Pb^{2+}$. The presence of these metal ions may deleterious to some procedures such as mass analysis and enzymatic reactions. The washing steps of the instant invention do not introduce appreciable amounts of metal ions.

Accordingly, in some embodiments, the present invention provides methods for cleaving and washing synthesized oligonucleotides comprising providing a solid substrate having attached thereto a linker-anchor-oligonucleotide moiety, washing the oligonucleotide on the substrate after synthesis and deprotection, cleaving the oligonucleotide from the linker-anchor-oligonucleotide moiety by a preferred reaction, and recovering the oligonucleotide, wherein the oligonucleotide is preferably purified and more preferably substantially pure and substantially free of metal ions.

Accordingly, in some embodiments, the present invention provides methods for cleaving and washing synthesized oligonucleotides comprising providing a solid substrate having attached thereto a linker-anchor1-oligonucleotide1-anchor2-oligonucleotide2 moiety, washing the sequence on the substrate after synthesis, cleaving oligonucleotide2 by selectively cleaving the anchor2 moiety, recovering oligonucleotide2, cleaving oligonucleotide1 by selectively cleaving the anchor1, recovering oligonucleotide 1, wherein the oligonucleotides are substantially pure and free of metal ions.

The present invention provides method of obtaining at least more than one oligonucleotide from a single synthesis by incorporation of anchor moieties of different cleavage requirements into the sequence. The use of a variety of anchor moieties is contemplated, including, but not limited to, those of the vicinal diol derivatives and dU in combination. dU can be first cleaved using UDG enzyme followed by amine treatment to release one oligonucleotide. The second anchor, vicinal diol derivative, is deprotected (i.e., O-TBDMS or O-fpmp can be deprotect by extensive acid treatment), rendering the diol moiety sensitive to basic conditions; the second oligonucleotide is released from substrate. Wherein the oligonucleotides are substantially pure and free of metal ions.

VI. PCR Using the Oligonucleotides Synthesized

Figure 11:
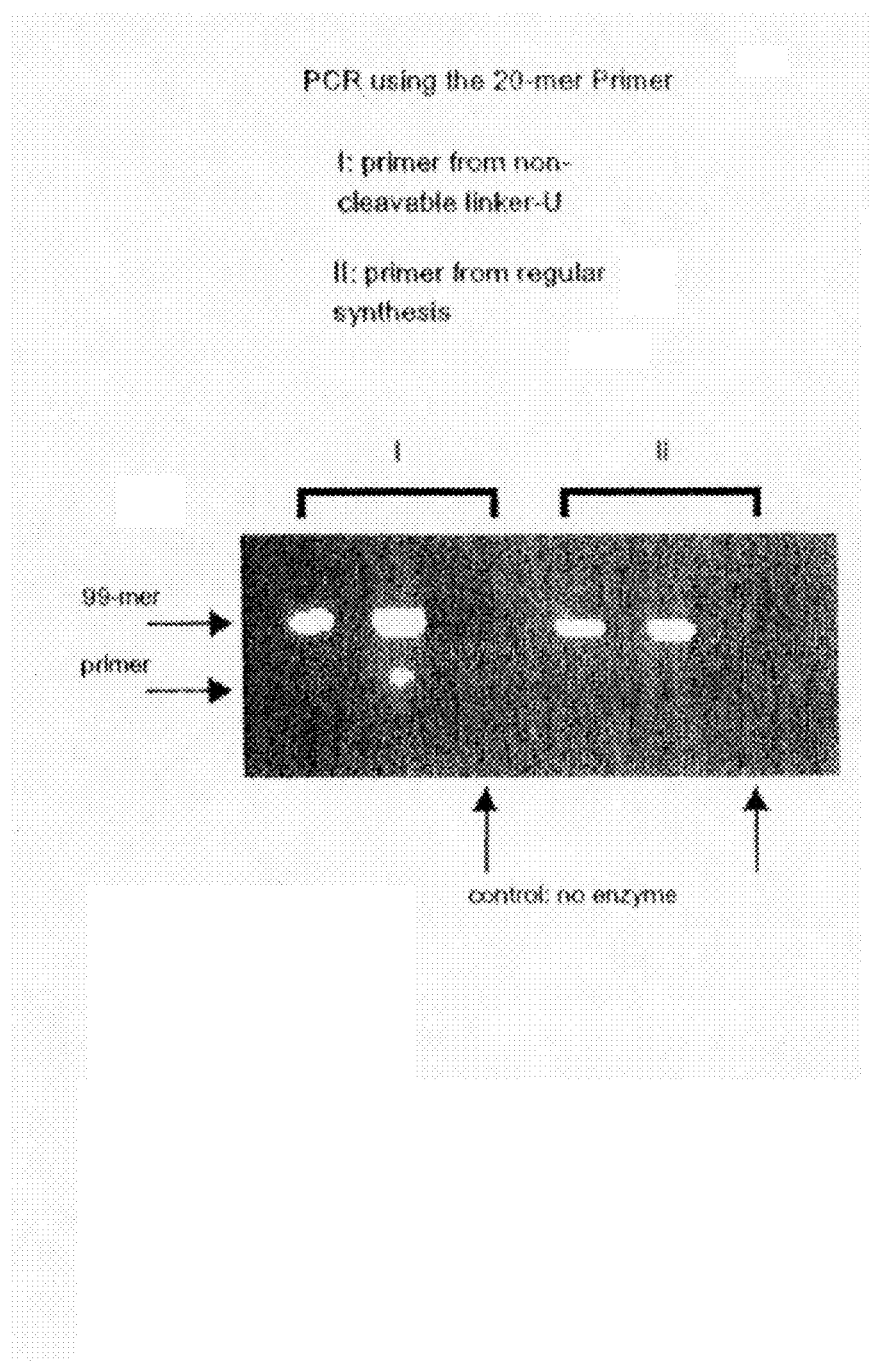
FIG. 11 presents the results of PCR experiments conducted with oligonucleotide primers synthesized on the supports of the present invention.

Accordingly, in some embodiments, the present invention provides methods for selective cleaving and recovering synthesized oligonucleotides in a form without contamination of the by products formed from deprotection of nucleobase and phosphate protecting groups. In some embodiments of the present invention, the U anchor moiety has its 2' or 3' OH available for polymer synthesis. The cleavage after the synthesis, deprotection and washing yields 3'-OH oligonucleotides and the 2',3'-cyclophosphate byproduct. One application of the 3'-OH oligonucleotides recovered after on surface deprotection and washing are DNA polymerase substrates used in PCR reactions to give desired DNA amplication (FIG. 11). The sequence generated using the stable diol linker without using any separate purification produced the same PCR results as the primers obtained from regular DNA synthesis.

VII. Ligation Using Oligonucleotides Synthesized

Figure 7:
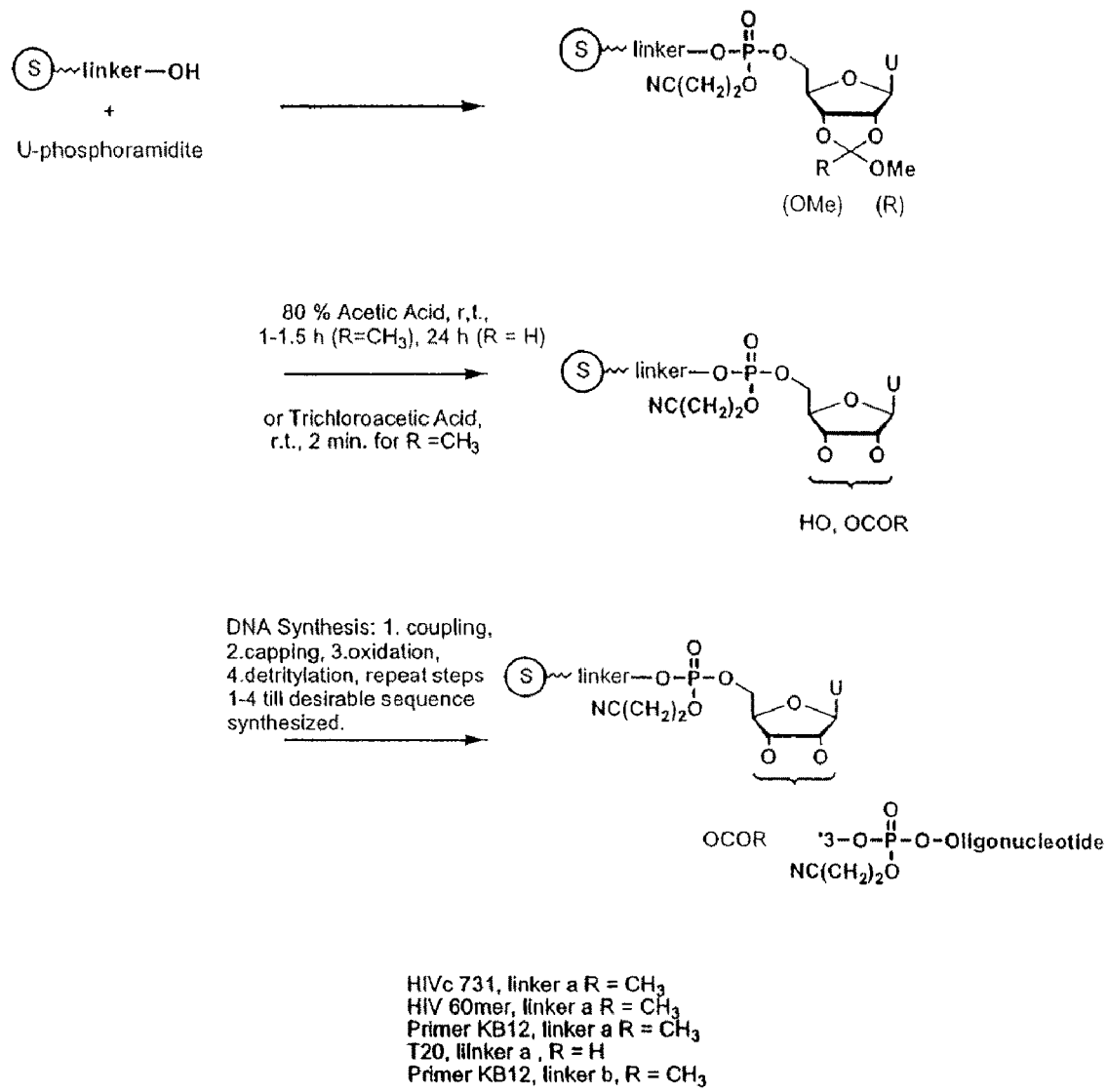
FIG. 7 presents a schematic depiction of the synthesis of an exemplary oligonucleotide.
Figure 8:
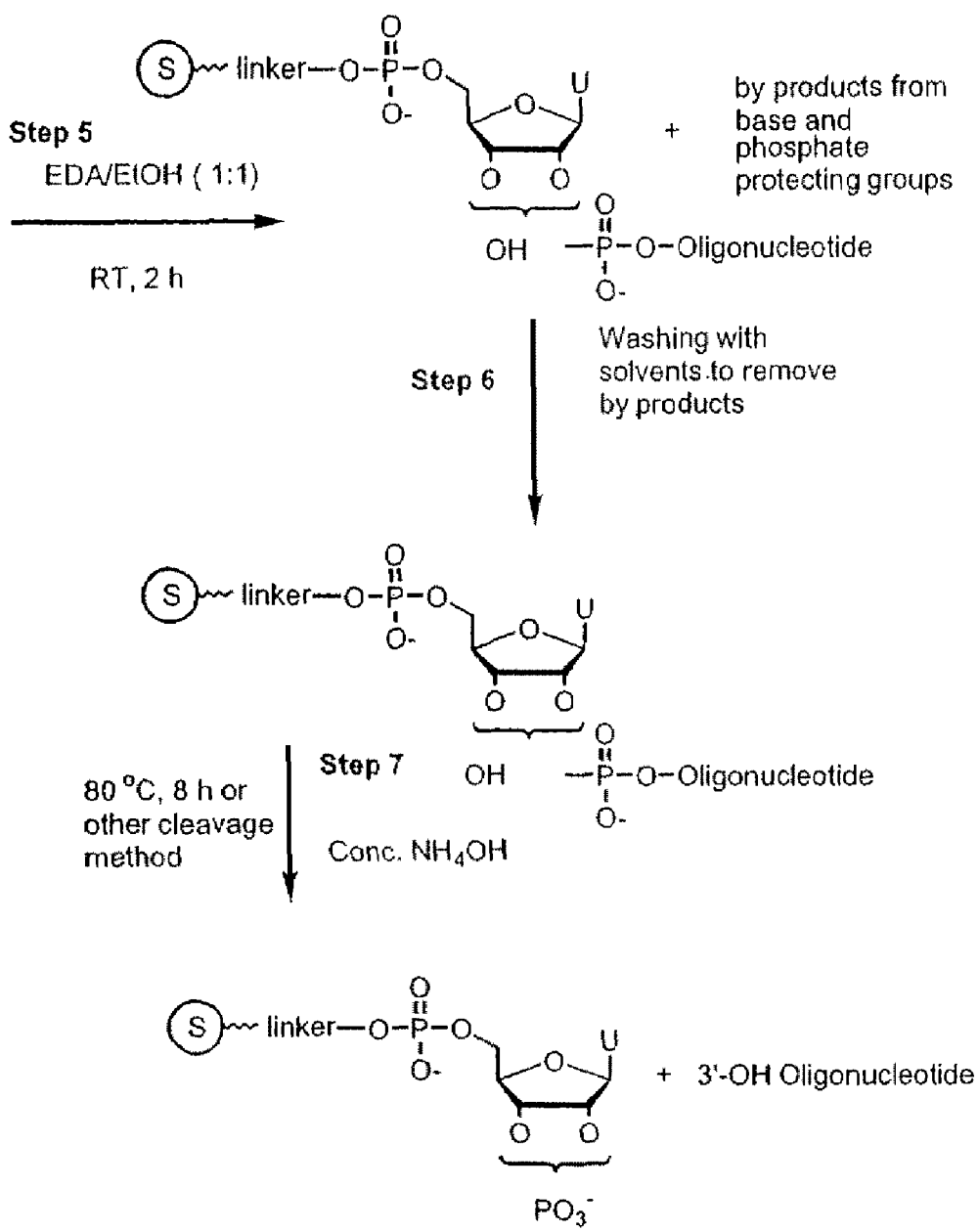
FIG. 8 presents a schematic depiction of deprotection and cleavage of an exemplary oligonucleotide.

Accordingly, in some embodiments, the present invention provides methods for selective cleaving and recovering synthesized oligonucleotides in a form without contamination of the by products formed from deprotection of nucleobase and phosphate protecting groups. These oligonucleotides can find applications in making large DNA fragments or synthetic genes. According to the present invention, an assembly of oligonucleotides, whose sequences are derived from a gene and which can form staggered partial duplexes, are synthesized using a stable linker, such as liner-U-2'(3')-OH (FIGS. 7 and 8). The syntheses, deprotection, washing and cleavage are performed as described, except for a 5'-phosphate is directly incorporated in the last step of synthesis using a compound of the structure:

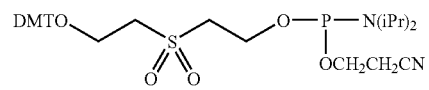

For high efficient production, these syntheses may be carried on a DNA synthesizer having parallel synthesis capability of 32 or more columns simultaneously or on a microchip where each reaction site can be utilized to generate different sequences (Gao et al. (2001) Nucleic Acids Res. 29, 4744-4750, cited herein entire reference). If is preferable to use the linker of higher density, such as the C8 alkenyl linker, to maximize the sequences generated per unit surface area.

In one embodiment of the present invention, 2',3'-O-methoxyethylideneuridine or 2',3'-O-methoxymethylideneuridine is prepared as described and converted to the 5'-phosphoramidite. The U linkage is formed by coupling the 5'-O-phosphoramidite U with the surface OH group through the phosphate bond formation (FIG. 7; step 2).

A typical synthesis process is as follows:

| Reaction | Reagent/Solvent | Special Steps |
|---|---|---|
| Detritylation | 3% TCA/CH$_2$Cl$_2$ or PGA- | Use of PGA-P in parallel synthesis |
| Wash | CH$_3$CN, CH$_3$CN | |
| Activation | tetrazole/CH$_3$CN | |
| Coupling | monomer/activator/CH$_3$CN | Special monomers, such as 5'-phosphoramidite-U can be incorporated |
| Wash | CH$_3$CN | |
| Capping (simultaneous) | 10% acetic anhydride/THF 10% MeIm/THF/Pyridine(8 | |
| Wash | CH$_3$CN | |

PGA-P is a photogenerated acid precursor, such as triarylsulfonium hexa(pentafluorophenyl)antimonite.

The synthesis of oligonucleotides is thus the same as conventional synthesis, but parallel synthesis on a microchip requires the in situ formation of photogenerated acid (PGA) rather than as opposed to acid in standard DNA synthesis chemistry (Gao et al. (2001) Nucleic Acids Res. 29, 4744-4750). The 2',3'-ortho ester of U is then hydrolyzed upon treatment of 80% HOAc/H$_2$O at r.t. for 1.5-2.5 h to free one of the vicinal OH groups (FIG. 7, step 3) to provide an anchor point for polymer growth.

The U-support prepared as described above, either on CPG in a column or on a microchip, is contacted with a 5'-DMT nucleophosphoramidite (A, C, G, or T, determined by the sequence synthesized) (FIG. 7, step 4). The coupling reaction results in formation of a U-2'(3')-O-[Phosphite]-O-3'-N (N is the DNA monomer) linkage and the sequence is terminated with a 5'-DMT group. Following the capping, the oxidation, and the detritylation reactions, a second 5'-DMT nucleophosphoramidite monomer can be coupled to the 5'-OH on the surface. The capping, oxidation, detritylation and coupling reactions are repeated till the desired oligonucleotides are synthesized. The oligonucleotide support is then treated with EDA/EtOH (1:1) to remove base and phosphate protecting groups as well as the 2'(3')-acetyl group (FIG. 8, step 5). Tests have been performed using $^{32}$P and T4 kinase to label the sequences potentially cleaved during the EDA treatment. However, electrophoresis analysis of the sample did not find any cleaved oligonucleotides. Thus, EDA does not cause hydrolysis of the 2'(3')-phosphate bond in U. After the deprotection reactions, the oligonucleotide surface is extensively washed with suitable solvents remove the small molecules formed from cleavage of the nucleobase and phosphate protecting groups (FIG. 8, step 6). Finally, the oligonucleotides are cleaved from the surface upon treatment with aqueous ammonium hydroxide, which hydrolyzes the 2'(3')-cyclic phosphate to produce oligonucleotides with a free 3'-OH (FIG. 8, step 7). The linker-U moiety is also cleaved in this reaction, but they do not cause any problem in the subsequent enzymatic reactions. The reaction volume recovered after cleavage reaction can be briefly evaporated to remove $NH_3$.

The oligonucleotides collected from either the solid support such as CPG or the microchips are directly used for ligation reactions without the need de-salt purification. A set of oligonucleotides are mixed and annealed using temperature gradients, treated with enzymes such as Taq or T4 ligase for ligation, which joins the nicks in the long sequences comprising of short, staggered partial duplex oligonucleotides aligned with juxtaposed 3'-hydroxyl and 5'-phosphoryl end groups in a nick-duplex structure. The optimal reaction condition for T4 DNA ligase is 50 mM Tris-HCl (pH 7.6), 10 mM MgCl2, 1 mM DTT, 1 mM ATP, 5% polyethyleneglycol-8000. In addition, T4 DNA ligase works adequately in the presence of phosphorylation buffer. Therefore, it is not necessary to remove the phosphorylation buffer if enzymatic phosphorylation is used. Taq DNA ligase can be used if the ligation needs to be done at higher temperature (~65° C.).

The large synthetic DNA is separated from the short segments, which may form due to non-specific hybridization, non-equivalent ligation efficiency, and other reasons. The large DNA duplex can be further purified using match repair enzymes. The sequence accuracy will be validated using sequencing and agarose gel analysis. Further cloning and protein expression are potential functional validation of the DNA sequence synthesized.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: amide linker: —$(CH_2)_3$NHCO$(CH_2)_3$X (X=OH, $NH_2$); ATP: adenosine triphosphate; Boc: ter-butyloxycarbonyl; $C_3$ linker: —$(CH_2)_3$X (X=OH, $NH_2$); $C_8$ linker: —$(CH_2)_8$X (X=OH, $NH_2$); CCD: charge coupled device; CPG: controlled porous glass; DCM: dichloromethane; DMF: dimethylformamide; DMT: 4,4'-dimethoxytrityl; DMT-Cl: 4,4'-dimethoxytritylcholoride; EDA: ethylene diamine; Fmoc: 9-fluorenylmethyloxycarbonyl; FR: fluorescence; FRE: fluorescence emission; PGA: photogenerated acid; SSPE: (6', 0.9 M NaCl, 0.066 M NaH2PO4, 0.012 M EDTA); TBE: (90 mM Tris-boric acid, pH 8.3, 2 mM EDTA; TCA: trichloroacetic acid; TEA: triethylamine; TEAA: triethylammonium acetate; TFA: trifluoroacetic acid; Tris: tris(hydroxymethyl)aminomethane; THF: tetrahydrofunan; eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin), r.t. (room temperature).

Example 1

This Example describes the derivatization of glass plates with an amide linker. Microscope cover/slide glass plates and microarray plates containing multiple sites were treated with hot piranha solution (concentrated $H_2SO_4$:$H_2O_2$, 50:50 v/v) for 15 min. The cleaned surface was thoroughly rinsed with $H_2O$ then EtOH, dried and immersed in a solution containing N-(3-triethoxysilylpropyl)-4-hydroxybutyramide (FIG. 1, amide linker, 1% v/v in 95% EtOH). The reaction was left at room temperature for a minimum of 1 h with gentle shaking. Upon completion of the reaction, glass plates containing the amide linker were rinsed thoroughly with 95% EtOH and cured at 100° C. under $N_2$ for 1 h. The derivatized plates were stored in a clean, dry container.

Example 2

This Example describes the derivatization of glass plates with an exemplary alkenyl linker ($C_8$). Microscope cover/slide glass plates and microarray plates containing multiple sites were treated with hot piranha solution (concentrated $H_2SO_4$:$H_2O_2$, 50:50 v/v) for 15 min. The cleaned surface was thoroughly rinsed with $H_2O$, acetone, $CH_2Cl_2$, then cyclohexane, and dried. The plates were placed in a sealable container containing 5 mM 7-octenyltrimethoxysilane, (FIG. 2, $CH_2$=$CH(CH_2)_6Si(OCH_3)_3$) in cyclohexane or 5 mM docosenyltriethoxysilane (FIG. 2, $CH_2$=$CH(CH_2)_{20}$Si$(OCH_2CH_3)_3$) in 4:1 cyclohexane:$CHCl_3$. The reaction was left at room temperature with gentle shaking for 16 h. Upon completion of the reaction, glass plates were rinsed thoroughly with cyclohexane and cured at 100° C. under $N_2$ for 1 h. The derivatized glass plates were placed in a 10 mL glass vial closed by a septum, separated by Teflon sheets. The container was purged with $N_2$ for 10 min, and 5 mL of 1 M $BH_3$.THF was introduced using $N_2$ and canulas. The borane reaction was allowed for 2 h at r.t. under gentle shaking. The solution was removed using $N_2$ positive pressure, and 5 mL of an oxidation solution was introduced. Three oxidation solutions were utilized: 0.1 M NaOH in 30% $H_2O_2$ for 3 min at room temperature (Netzer, L., Iscovivi, R., Sagiv, J. Adsorbed monolayers versus Langmuir-Blodgett monolayers—why and how? I. From monolayer to multilayer, by adsorption. *J. Thin Solid Films* (1983) 99, 235-241; Netzer, L., Iscovivi, R., Sagiv, J. Adsorbed monolayers versus Langmuir-Blodgett monolayers—why and how? II. Characterization of built-up films constructed by stepwise adsorption of individual monolayers. *J. Thin Solid Films* (1983) 99, 67-76; Netzer, L., Sagiv, J. A new approach to construction of artificial monolayer assemblies. *J. Am. Chem. Soc.* (1983) 105, 674-6; Wasserman, S. R., Tao, Y.-T., and Whitesides, G. M. Structure and reactivity of alkylsiloxane monolayers formed by reaction of alkylrichlorosilanes on silicon substrates. *Langmuir* (1989) 5, 1074-1087); 3 M NaOAc in 30% $H_2O_2$, pH 7.5 for 10 hours at room temperature; and 1:10 30% $H_2O_2$:THF at 0° C. for 24 h. The reaction solution was then removed and the plates were rinsed with $H_2O$, EtOH, dried and stored in a clean, dry container

Example 3

This Example describes the derivatization of glass plates. Microscope cover/slide glass plates and microarray plates containing multiple sites were treated with hot piranha solution (concentrated $H_2SO_4$:$H_2O_2$, 50:50 v/v) for 30 min. The cleaned surface was thoroughly rinsed with EtOH, $CH_2Cl$, and toluene, and dried with a stream of ultra high purity $N_2$. The plates were placed in a closed container containing 43 mM 3-aminopropyltriethoxysilane (FIG. 2) in toluene. The reaction was heated to 60° C. for 4 min. Upon completion of the reaction, glass plates were rinsed five time with toluene and dried with $N_2$.

Example 4

This Example describes the analysis of contact angles of derivatized glass plates. Contact angles were measured at r. t. by application of static drops (4-10 μL) of deionized water to linker derivatized substrate surfaces with a micropipetter. The measurements were made visually on both sides of the drops using a Zisman type goniometer equipped with a video camera. Tangent to the drop at its intersection with the surface determined contact angle θ. The advancing contact angle, $\theta_a$, was taken as the maximum contact angle observed as the drop size was incrementally increased without an increase in the contact area. The receding contact angle, $\theta_r$, was taken as the minimum contact angle observed as the drop size was decreased with a decrease in the contact area. Average values of a least three measurements performed on each substrate were reported. These measurements are shown in Table 1.

TABLE 1

| Contact Angle of Monolayer Linker on Glass Substrate | | |
|---|---|---|
| Linker (Terminus group) | Advancing (°) | Receding (°) |
| Amide Linker (OH) | 54 | 44 |
| $C_8$($CH_2$=CH—) | 92 | 83 |
| $C_8$(OH)[a] | 63 | 53 |
| $C_8$(OH)[a] | 69 | 55 |
| $C_8$(OH)[a] | 66 | 55 |
| $C_{22}$($CH_2$=CH—) | 100 | 74 |
| $C_{22}BH_3$/NaOH(OH)[b] | 92 | 58 |
| $C_3$($NH_2$) | 54 | 30 |
| $C(CH_3)_2C_2(NH_2)$ | 55 | 52 |
| $C(CH(CH_3)_2)_2C_2(NH_2)$ | 65 | 54 |

[a]Hydroxyl group was introduced by oxidizing the terminus double bond using $BH_3$/THF/$H_2O_2$, $BH_3$/NaOAc, or $BH_3$/NaOH, correspondingly.
[b]Hydroxyl group was introduced by oxidizing the terminus double bond using $BH_3$/NaOH.

Example 5

This Example describes oligonucleotide synthesis on glass plates derivatized with the $C_8$ or amide linkers. The amide or $C_8$ linker derivatized glass plates were divided into strips of ~30 mm² and synthesis was performed in a circular column. The glass plates were held in the direction of flow by two pieces of Teflon inserts in the column. The surface of the inserts was caved to allow contact of reaction solution with the surface of glass plates. The oligonucleotides synthesis used an automated DNA synthesizer (Expedite 8909) and protocols that were modified from that of standard 1 μmol synthesis. A typical protocol for such a synthesis is given below (Table 2). The DMT-monitor on the synthesizer was turned off because the amount of DMT$^+$ was too little to be measured. Monomers were DMT-dA(N6bz), DMT-dC (N4bz), DMT-dG(N2ib), and DMT-T.

TABLE 2

| Synthesis Protocol of DNA Oligonucleotides on Glass Plates | | | | | | |
|---|---|---|---|---|---|---|
| Reaction | Reagent | Conc (mM) | # Pulse | Vol. (ml) | Time Set | Time (sec) |
| Detritylation | 3% TCA/$CH_2Cl_2$ | 29.5 | 110 | 1.760 | | 39.6 |
| wash A | $CH_3CN$ | na | 170 | 2.720 | | 37.4 |
| Wash | $CH_3CN$ anhydrous | na | 80 | 1.280 | | 28.8 |
| Coupling | Activator: tetraazole/$CH_3CN$ | 450.0 | 35 | 0.560 | | 12.6 |
| Mono + activator | activator | 450.0 | 50 | 0.800 | | 18.0 |
| (simultaneous) | monomer + activator | 50.0 | 50 | 0.800 | | |
| Wash | $CH_3CN$ anhydrous | na | 8 | 0.128 | | 2.9 |
| wash A | $CH_3CN$ | na | 130 | 2.080 | | 28.6 |
| Oxidation | $I_2$/THF/pyridine/$H_2O$ | 20.0 | 60 | 0.960 | | 21.6 |
| Oxidation | $I_2$/THF/pyridine/$H_2O$ | 20.0 | 10 | 0.160 | 15.000 | 15.0 |
| wash A | $CH_3CN$ | na | 120 | 1.920 | | 26.4 |
| Capping | 10% acectic anhydride/THF | 1057.8 | 50 | 0.800 | | 18.0 |
| (simultaneous) | 10% Melm/THF/Pyridine(8/1) | 1254.6 | 50 | 0.800 | | |
| Capping | 10% acectic anhydride/THF | 1057.8 | 10 | 0.160 | 15.000 | 15.0 |
| (simultaneous) | 10% Melm/THF/Pyridine(8/1) | 1254.6 | 10 | 0.160 | | |
| wash A | $CH_3CN$ | na | 140 | 2.240 | | 30.8 |

Example 6

This Example describes oligonucleotide synthesis on glass plates derivatized with the $C_8$ or amide linkers. Oligonucleotide synthesis is performed with DMT-tri(hexaethylene glycol) phosphoramidite, DMT-dA(Nbz), DMT-dC(Nbz), DMT-dG(Nib), and DMT-T phosphoramidite, and 5'-MeO-T phosphoramidite as the co-coupling agent of DMT-T phosphoramidite.

DMT(O(CH$_2$)$_2$)$_3$OP(OCH$_2$CH$_2$CN)(NCH(CH$_3$)$_2$)$_2$ (spacer, DMT-hexaethyleneglycosyl phosphoramidite) (FIG. 1) was prepared using the same reaction conditions as tritylation and phosphitylation of DNA nucleoside. 5'-MeO-T (Kowollik, G., Gaertner, K., and Langen, P. (1966) 5'-O-methylthymidine. *Angew. Che. Internat. Edit.* 5, 735-736) and 5'-CH$_3$-T (Sekine, M., and Nakanishi, T. (1990) Facile synthesis of 3'-O-methylthymidine and 3'-dexoythymidine and related deoxygenerate thymidine derivative: A new method for selective deoxygenation of secondary hydroxy groups. *J. Org. Chem.* 55, 924-928) (both are chain terminators) (FIG. 2) were prepared according the procedures described in the literature. The corresponding phosphoramidites were prepared in a similar manner as T phosphoramidite preparation.

The amide or $C_8$ linker derivatized glass plates were divided into strips of ~30 mm$^2$ and synthesis was performed in a circular column. The glass plates were held in the direction of flow by two pieces of Teflon inserts in the column. The surface of the inserts was caved to allow contact of reaction solution with the surface of glass plates. The oligonucleotides synthesis used an automated DNA synthesizer (Expedite 8909) and protocols that were slightly modified from that of standard 1 μmol synthesis (Table 2). The DMT-monitor on the synthesizer was turned off because the amount of DMT$^+$ was too little to be measured. In some synthesis, the first few steps of coupling were performed without capping of the failure sequences. The synthesis steps used a mixture of coupling and co-coupling agents, such as T and 5'-MeO-T phosphoramidites are indicated by X, where the coupling and co-coupling agents (e.g. a terminator) are in various ratios; ratio typical was 1:1-1:10. Examples of the sequences synthesized on glass plates were given below (S=spacer; 3'-tail=5'-TTTTT, 5'-XTTTTT, 5'-TTTXTT, 5'-SSTTTTT, 5'-XSSTTTTT, 5'-SXSTTTTT, or 5'-SSXTTTTT).

```
                                            (SEQ ID NO: 1)
15-mer: 5'-TATGTAGCCTCGGTC-3'-tail (SEQ ID NO: 2)
16-mer: 5'-CTCCTACGGGAGGCAG-3'-tail (SEQ ID NO: 3)
24-mer: 5'-GTCACCATGTTGACTCACCATGTC-3'-tail (SEQ ID NO: 4)
41-mer: 5'-TGTTGACTCACCATGTCGTCACCATGTTGACTCACCATG
        TC-3'-tail
```

Example 7

Figure 3:
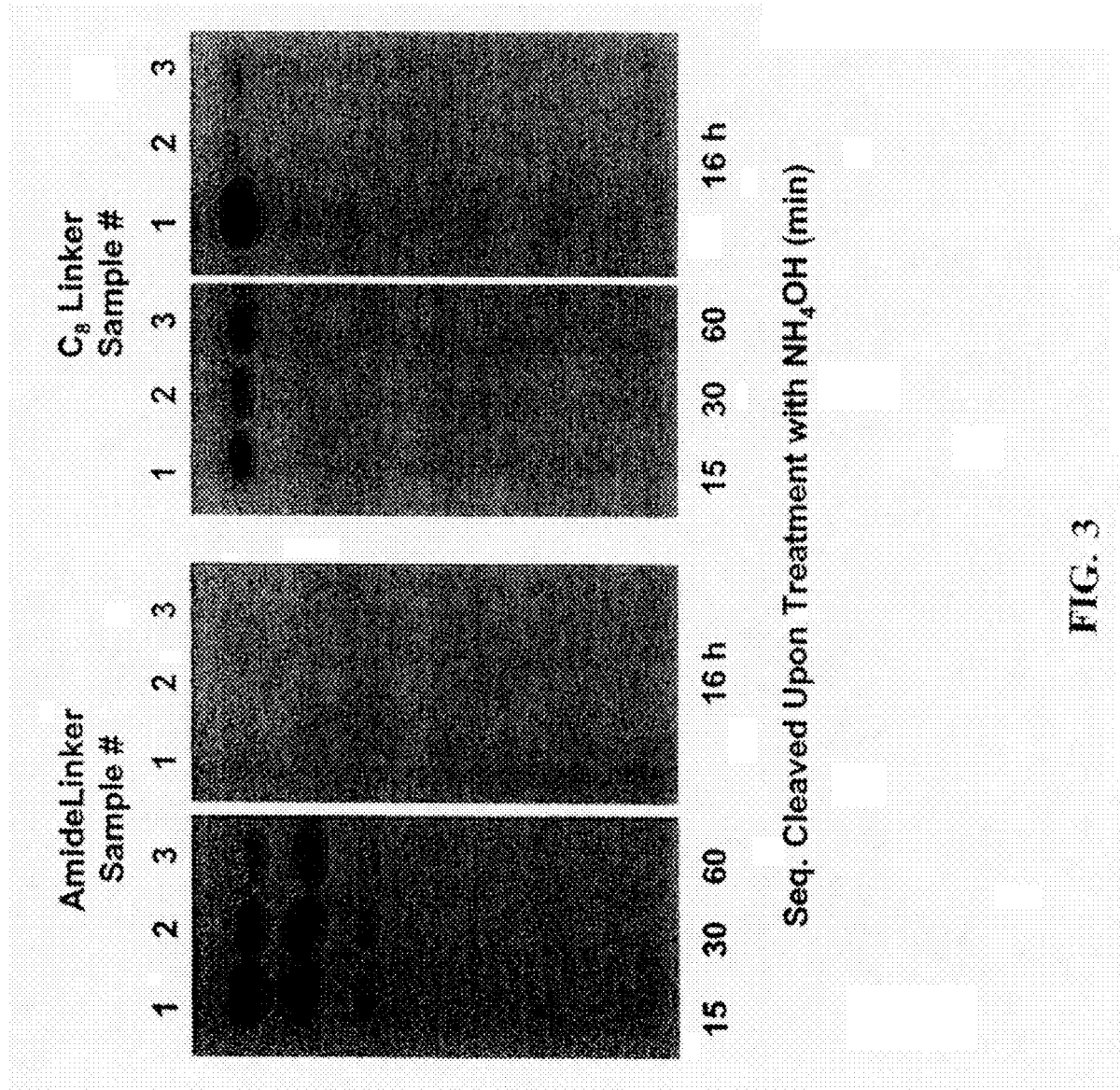
FIG. 3 displays electrophoresis gel profiles of $T_{10}$ cleaved from glass plates at 15, 30 and 60 min upon treatment with conc. aq. $NH_4OH$. The $T_{10}$ with amide linker is shown on the left panel and the $T_{10}$ with $C_8$ linker is shown on the right panel.

This Example describes the time dependent ammonolysis of oligonucleotides from the solid support. The glass plates (ca. 2 mm$^2$) containing $T_{10}$ in eppendorff tube were treated with conc. NH$_4$OH (50 μL) at r.t. At 15 and 30 min, the solution was removed from the tube. The glass plates were treated with NH$_4$OH (50 μL) again for 16 h at r. t. These solution samples were vacuum dried and redissolved in H$_2$O (10 μL for each 1 mm$^2$ plate). A portion of the sample (3 μL) was labeled with γ-$^{32}$P-ATP (5 μCi, 3000 Ci/mmole) using T4 polynucleotide kinase (1 u) and the conditions recommended by the manufacturer (Gibco). $^{32}$P-labeled oligonucleotides (4 μL) were mixed with formamide (6 μL) before loading onto a gel containing 20% acrylamide/bisacrylamide (29/1) in 7 M urea. Gels in 1×TBE (90 mM Tris-Boric acid, pH 8.3, 2 mM EDTA) were subjected to electrophoresis at 55 V/cm for ~1.5 h at room temperature. $^{32}$P exposure on an X-ray film (Kodak) produced gel films. The intensities of the gel bands were derived using the Image Pro program (Media Imagenics) after scanning digitization of the gel film. FIG. 3 displays electrophoresis gel profiles of $T_{10}$ cleaved from glass plates at 15, 30 and 60 min upon treatment with conc. aq. NH$_4$OH. The $T_{10}$ with amide linker is shown on the left panel and the $T_{10}$ with $C_8$ linker is shown on the right panel.

Example 8

Figure 4:
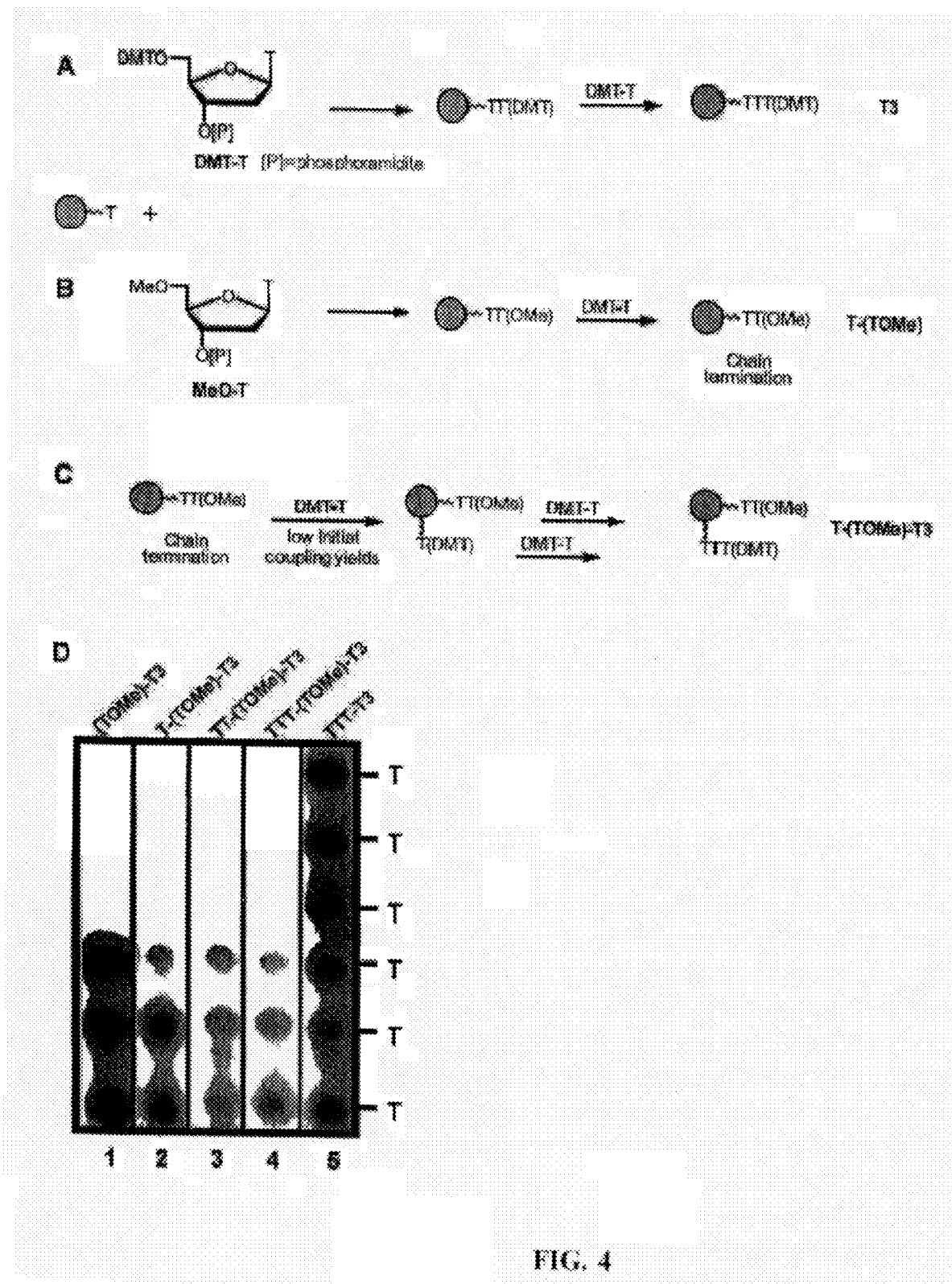
FIG. 4 presents results of an assay of oligonucleotide synthesis using a termination nucleophosphoramidite, 5'-MeO-T, to probe the presence of available sites for coupling with a phosphoramidite at different reaction stages. (A) Regular $T_3$ synthesis on glass plates. (B) Illustration of the use of termination monomer. T on glass plate is coupled with MeO-T, resulting in the formation of a terminated dimer T-T(OMe), which can not undergo further chain growth. (C) Illustration of the hypothesis for reaction with more hindered surface sites in several continued reaction cycles. (D) $^{32}$P-gel electrophoresis analysis of the experiments using the termination 5'-MeO-T at different stages of oligonucleotide synthesis.

This Example describes an assay of oligonucleotide synthesis using a termination nucleophosphoramidite, 5'-MeO-T, to probe the presence of available sites for coupling with a phosphoramidite at different reaction stages. The sequences terminated with 5'-MeO-T are not observed, since they cannot be $^{32}$P labeled at the 5'-OH using T4 polynucleotide kinase. The results of these assays are illustrated in FIG. 4. (A) Regular $T_3$ synthesis on glass plates. (B) Illustration of the use of termination monomer. T on glass plate is coupled with MeO-T, resulting in the formation of a terminated dimer T-T(OMe), which can not undergo further chain growth. (C) Illustration of the hypothesis for reaction with more hindered surface sites in several continued reaction cycles. If these sites exist, oligonucleotides can be synthesized even after applying MeO-T in the coupling step. (D) $^{32}$P-gel electrophoresis analysis of the experiments using the termination 5'-MeO-T at different stages of oligonucleotide synthesis. Lane 1. Sequences from a synthesis which used MeO-T in the first step of coupling, followed by coupling with DMT-T. The sites that failed to couple with MeO-T would produce regular sequences, such as $T_3$. This sequence is clearly present in a significant ratio along with $T_2$ and $T_1$ fragments. Lane 2. Sequences from a synthesis which used MeO-T at the second step of coupling, followed by coupling with DMT-T. The monomer T sites that failed to couple with MeO-T would produce regular sequences, such as T-$T_3$ or $T_4$. In this experiment, little $T_4$ was observed. The surface OH sites that failed to couple with DMT-T in the first step would also be responsible for the observed $T_{1-3}$ sequences. Lane 3. Sequences from a synthesis which used MeO-T at the third step, followed by coupling with DMT-T. $T_5$ and $T_4$ were not observed. There are diminished amounts of overall sequences and short $T_n$ fragments. Lane 4. Sequences from a synthesis which used MeO-T at the fourth step, followed by coupling with DMT-T. Only minor $T_{1-3}$ were observed. Lane 6. Regular synthesis of $T_6$ as a control.

Example 9

This Example describes hybridization of complementary sequences to the synthesized sequences. The target sequences (100-200 nM) containing fluorescein label were dissolved in a 6×SSPE solution (50-200 μL, 1 M NaCl, 66 mM sodium phosphate, 6 mM EDTA, pH 7.4) and applied to the glass plate or a chip containing probe sequences. The experiments were performed under a cover slip at r. t. or a temperature suitable for the given set of target and probe sequences for 2 h or longer. The plates were then washed twice with 6×SSPE, spin dried, and the fluorescence image was taken using a cooled CCD camera (Apogee Instruments). A 200 W Xenon lamp was used as the light source. Fluorophore excitation and detection were 475 and 535 nm, respectively. Fluorescence images were processed and analyzed using the Image Pro (Media Cybernetics), ScanAlyze2 (http://rana.Stanford.EDU/software/), and the Excel (Microsoft) programs. Fluorescence intensities were reported after baseline correction and averaging over redundant data points.

Example 10

Figure 5:
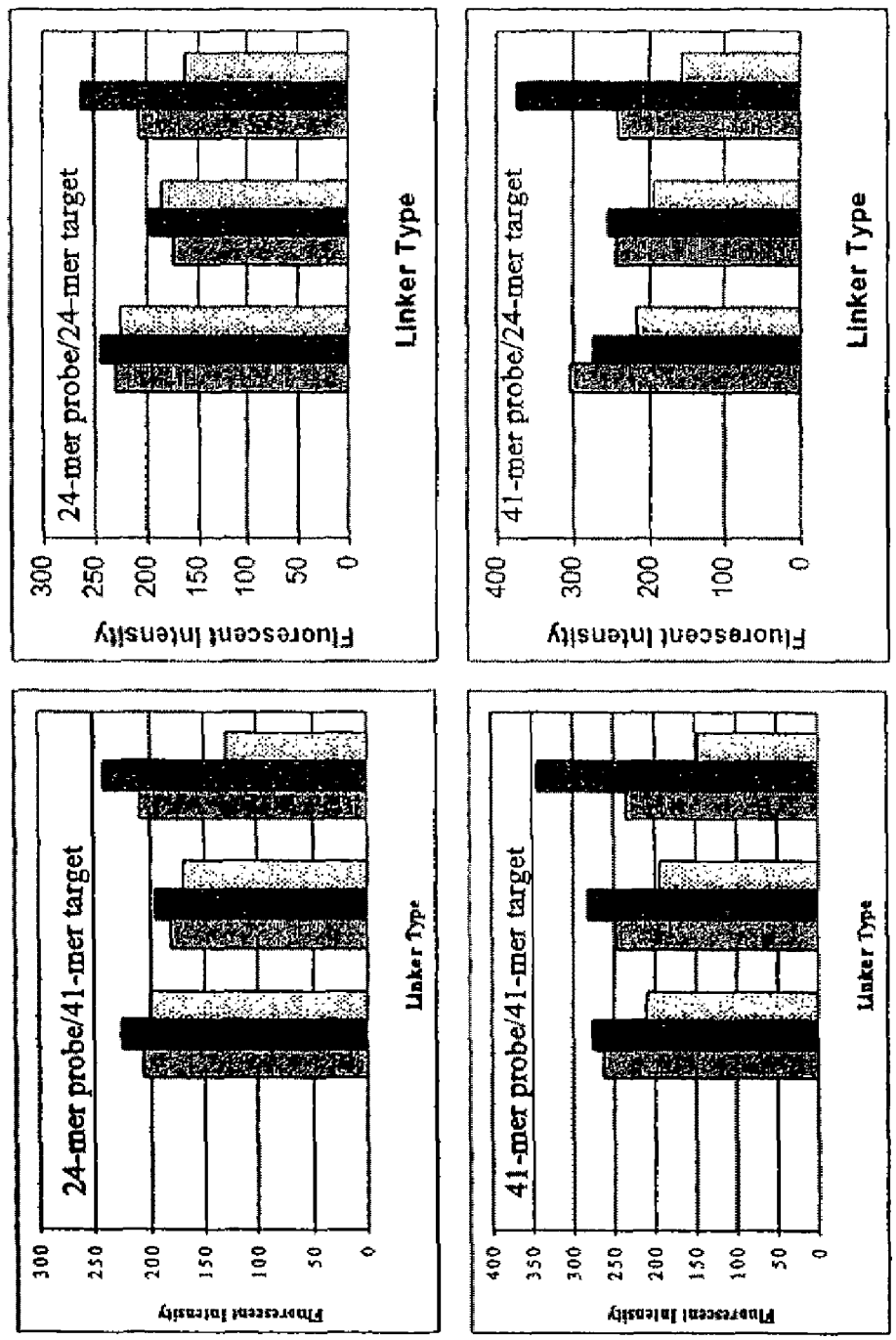
FIG. 5 presents a comparison of the probe sequences synthesized using the amide and C8 linkers and used for three time hybridization experiments.

This Example describes hybridization of complementary sequences to the synthesized sequences. The glass plates containing the 24-mer and the 41-mer probes were hybridized with target sequences as described and were then washed with low salt buffer solution containing NaCl (5 mM) and $NaH_2PO_4$ (5 mM), pH 7.0 until the fluorescence intensity reading was comparable to background of the glass plates. The hybridization and image acquisition were repeated multiple times. The comparison of the probe sequences synthesized using the amide and C8 linkers and used for three time hybridization experiments is shown in FIG. 5.

Example 11

This Example describes synthesis on CPG using the $C_8$ and amide linkers.

(a) $CPG-O_3Si(CH_2)_8OH$ ($C_8$ Linker)

CPG (500 Å, 500 mg or 2000 Å, 500 mg) in 2.5% 7-octenyltrimethoxysilane/cyclohexane was shaken at rt for 24 h, then washed with cyclohexane, dried at 100° C. for 0.5 h in vacuo. The derivatized CPG (100 mg) was treated with borane/THF (1.0 M, 2.5 mL) at rt under $N_2$ with occasional shake for 3 h. CPG was washed with THF. Unreacted borane/THF was destroyed with ice $H_2O$. CPG was then treated with 0.1 M NaOH/30% $H_2O_2$ (1:1) at rt for 3 min. The solution was removed by filtration. CPG was washed with $H_2O$, EtOH, and acetone, and dried under vacuum.

(b) $CPG-O_3Si(CH_2)_3NHCO(CH_2)_3OH$ (Amide Linker)

CPG (500 Å, 500 mg) in 2% $(EtO)_3Si(CH_2)_3NHCO(CH_2)_3 OH$/95% EtOH was shaken at rt for ~12 h, washed with 95% EtOH and diethyl ether, and cured on hot plate (~100° C.) for 1 h with $N_2$.

CPG loading: The linker derivatized CPG (10 mg) in dry pyridine (0.5 mL) was shaken with DMTCl (10 mg) at rt for 3 h and then washed, in sequence, with pyridine, sat. $NaHCO_3$ in ice $H_2O$ (1:1), $H_2O$, EtOH, $CH_2Cl_2$. The tritylated CGP was then treated with 2% TCA for 2 min and a portion of the resultant $DMT^+/CH_2Cl_2$ solution was measured at 503 nm ($\epsilon$=76 mM $cm^{-1}$). Calculation was performed to obtain the loading of CPG (μmol linker-OH sites/g). The results were 20 μmol/g for CPG-amide linker (500 Å), 108 μmol/g for CPG-$C_8$ linker (500 Å), and 22 μmol/g for CPG-$C_8$ linker (2000 Å).

Example 12

Figure 2:
FIG. 2 provides exemplary chemical structures for a fluorescein tag, a chain terminator (co-coupling agent) and an anchor.
Figure 2:
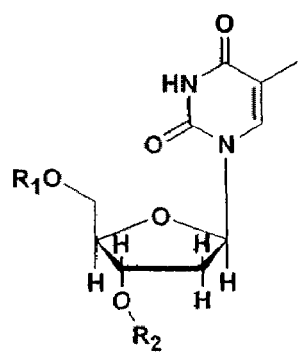
Figure 2:
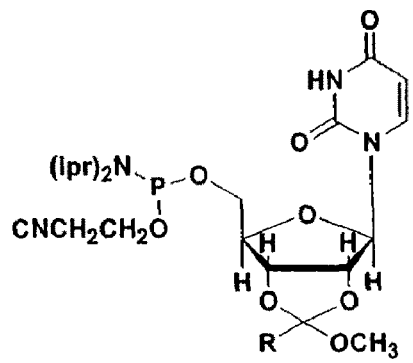
Figure 6:
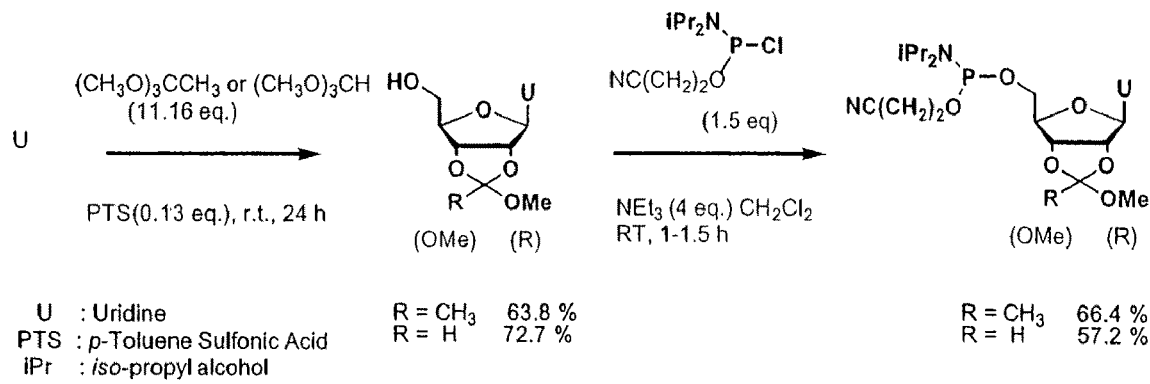
FIG. 6 presents a schematic depiction of the synthesis of an exemplary anchor moiety.

This Example describes synthesis on CPG using $C_8$ and amide linkers, wherein the first coupling is with a uridine moiety. 2',3'-O-methoxyethylideneuridine or 2',3'-O-methoxymethylideneuridine was prepared according to literature (Fromageot, H. P. M., Griffin, B. E., Reese, C. B., Sulston, J. E. The synthesis of oligoribonucleotides-III. Monoacylation of ribonucleosides and derivatives via orthoester exchange. *Tetrahedron* 1967, 23, 2315-2331) (FIG. 6). These compounds were converted to 5'-phosphoramidites using a similar procedure to that for preparation of DNA nucleophoramidites (FIG. 2). The 5'-U phosphoramidite was freshly dissolved in $CH_3CN$ (50 mM) and placed on a DNA synthesizer for automated synthesis of oligonucleotides.

Oligonucleotide synthesis used derivatized CPG (Table 3) containing stable amide or $C_8$ linker and was performed in a 1 μmol column. 5'-U phosphoramidite was coupled to the linker terminus OH group using the RNA synthesis protocol including coupling, capping and oxidation steps (FIG. 7). The 2',3'-ortho ester of U was hydrolyzed after treatment of 80% $HOAc/H2O$ (1 mL) at r.t. for 1.5-2.5 h (FIG. 7). The CPG was washed with cold $H_2O$, saturated ice $NaHCO_3/H_2O$ (1:1), cold $H_2O$, and $CH_3CN$, dried in vacuo. The linker-5'-U derivatized CPG (Table 3) was loaded into a 1 μmol column on a DNA synthesizer. Oligonucleotide sequences were synthesized using standard synthesis protocols.

Upon completion of synthesis, the sequence bound CPG was treated with EDA/EtOH (1:1, v/v, 1 mL) at r.t. for 2 h, washed with 95% EtOH and $CH_3CN$, and dried in vacuo to give protecting group free sequence bound CPG (FIG. 8).

The deprotected or protected sequence bound CPG was treated with one of the following conditions: (i) $NH_4OH$ (aq. 0.5 mL) at 80° C. for 8 h; (ii) or conc. $NH_4OH/40\%$ $MeNH_2$ (1:1) at 80° C. for 3 h; (iii) 40% $MeNH_2/TEA/EtOH$ (1:1:0.2) at 80° C. for 3 h; (iv) conc. $NH_4OH/TEA/EtOH$ (1:1:0.6) at 80° C. for 3 h. The solution containing cleaved oligonucleotides (3'-OH) was dried by speed-vac. The residue was dissolved in $H_2O$ and centrifuged. The aqueous solution was analyzed by HPLC. The analysis result showed that conc. $NH_4OH$ at 80° C. for 8 h is a better condition for cleaner cleavage and that C8 linker produced three times more oligonucleotides than that produced using the amide linker on the same amount of CPG (Table 3). The primer KB12 sequences synthesized using the stable amide linkers or the regular succinyl linker gave the same HPLC retention times.

Figure 9:
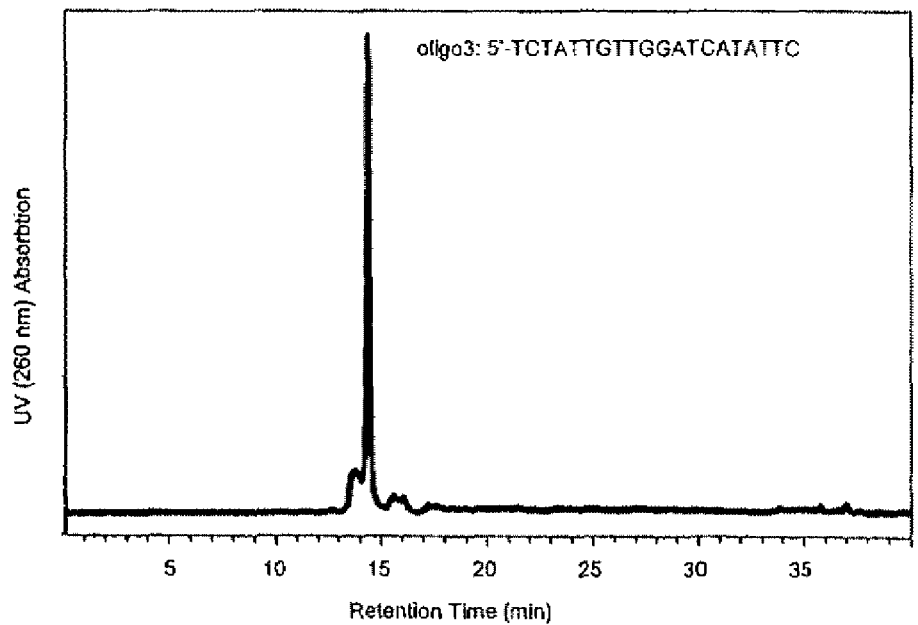
FIG. 9 presents HPLC data for oligonucleotides (SEQ ID NOS: 5 and 7) synthesized on the supports of the present invention.
Figure 9:
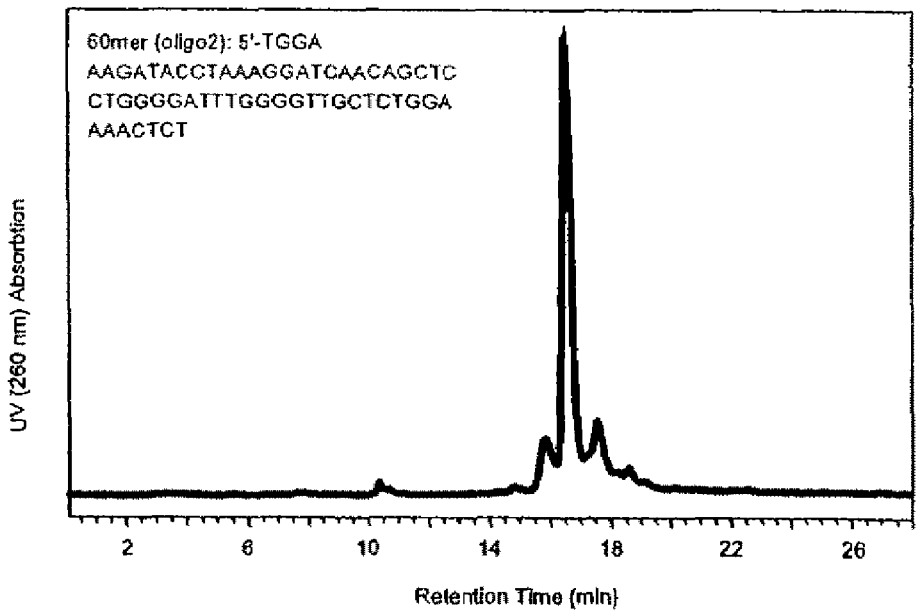

HPLC was performed on a $C_{18}$ reverse phase column (Waters) using 50 mM TEAA in $CH_3CN$. Flow rate was 1 mL/min. HPLC results are shown in FIG. 9. Mass data were obtained from a MALDI-TOF instrument (Profelix, Bruker) in negative mode and these results are given in Table 3.

TABLE 3

Summary of Oligonucleotide Synthesis on CPG Using Non-cleavable Linkers Coupled to 5'-Phosphoramidite-U

| No | CPG | Linker | Sequence On Support (5'-3')[a] | Deprotection | Cleavage from Support | Detritylation | Cleavage from U | Amount Product (OD) | Appli- cation | MS (calc.; obs.) |
|---|---|---|---|---|---|---|---|---|---|---|
| 1 | 500 Å, 10 mg, 1 umol | C8-rU | 5'-DMT-primer KB12, 20-mer | EDA/EtOH (1:1) rt, 2 h | ammonia (aq), rt, 48 h | 80% AcOH, rt., 1 h | ammonia (aq), 80 C., 8 h | 38 | | |

TABLE 3-continued

Summary of Oligonucleotide Synthesis on CPG Using
Non-cleavable Linkers Coupled to 5'-Phosphoramidite-U

| No | CPG | Linker | Sequence On Support (5'-3')[a] | Cleavage from Deprotection | Cleavage from Support | Detrit-ylation | Cleavage from U | Amount Product (OD) | Appli-cation HPLC | MS (calc.; obs.) |
|---|---|---|---|---|---|---|---|---|---|---|
| 2 | 2000 A, 23 mg, 0.5 umol | C8-rU | 5'-DMT-primer KB12, 20-mer | EDA/EtOH (1:) rt, 2 h | ammonia (aq), rt, 48 h | 80% AcOH, rt., 1 h | ammonia (aq), 80 C., 8 h | 23 | fig PCR | 6084; 6065 |
| 3 | 500 A, 10 mg, 1 umol | C8-rU | 5'-DMT-primer KB12, 20-mer | EDA/EtOH (1:1) rt, 2 h | ammonia (aq), rt, 48 h | 80% AcOH, rt., 1 h | ammonia (aq), 80 C., 8 h | 34 | | |
| 4 | 2000 A, 23 mg, 0.5 umol | C8-rU | 5'-OH HIVs 60mer | | | | half of #4, ammonia (aq), 80 C., 8 h | 75 | fig | 18591; 18532 |
| 4a | from #4 0.25 umol | C8-rU | 5'-FR HIVs 60mer | EDA/EtOH (1:1) rt, 2 h | | | ammonia (aq), 80 C., 8 h | | fig hybridi-zation | |
| 4b | from #4, 0.25 umol | C8-rU | 5'-FR HIVs 60mer | EDA/EtOH (1:1) rt, 2 h | | | enzyme purification then ammonia (aq), 80 C., 8 h | | fig hybridi-zation | |
| 6 | 500 A, 25 mg 0.5 umol | amide | 5'OH-primer KB12 20-mer | EDA/EtOH (1:1) rt, 2 h | | | ammonia (aq), 80 C., 8 h | 28 | | |
| 6a | from #6, 500 A | amide | 5'-OH-primer KB12, 20-mer | | | | ammonia (aq), 80 C., 8 h | | | |

[a] primer KB12: 5'-TCTATTGTTGGATCATATTC (SEQ ID NO: 5);
HIVs60mer 5'-TGGAAAGATACCTAAAGGATCAACAGCTCCTGGGGATTTGGGGTTGCTCTGGAAAACTCT (SEQ ID NO: 6)

Example 13

Figure 10:
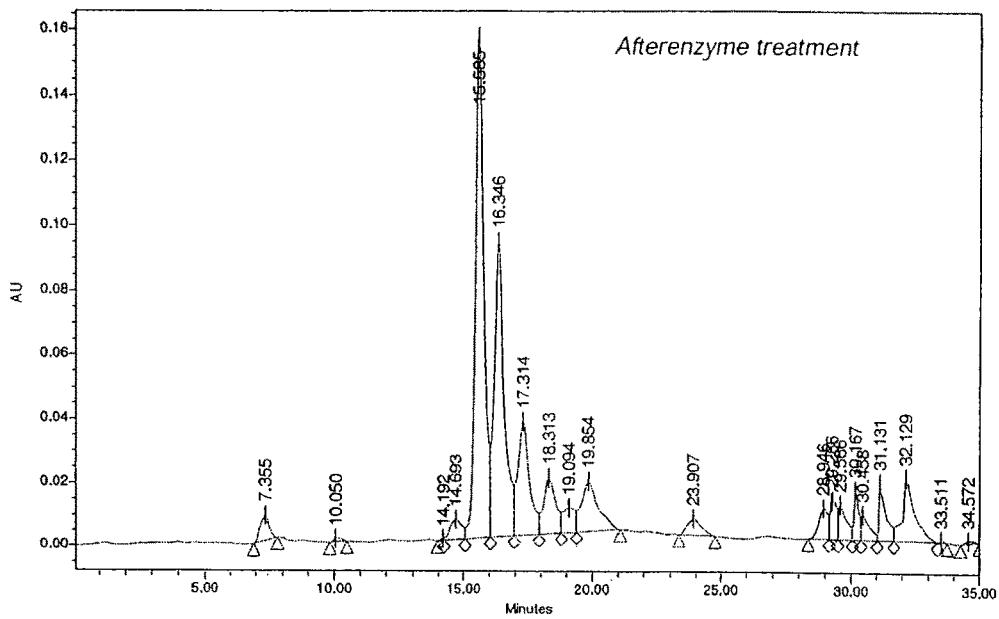
FIG. 10 presents HPLC data for the enzyme purified sequence cleaved from CPG.
Figure 10:
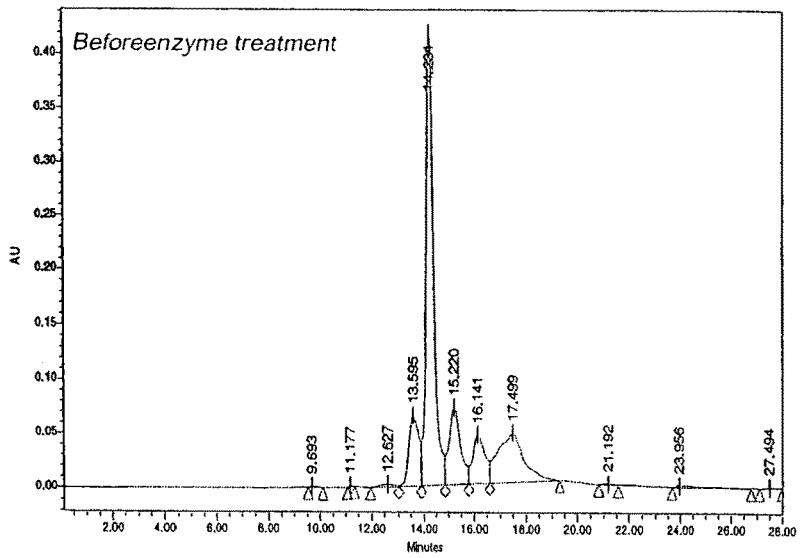

This Example describes purification of the synthesized oligonucleotides with enzymes. The synthesis of HIVs60mer, 5'-FR-TGG AAA GAT ACC TAA AGG ATC AAC AGC TCC TGG GGA TTT GGG GTT GCT CTG GAA AAC TCT (SEQ ID NO: 7) (FR=diisobutyryl-4(5)-CO-fluorescein-NH(CH$_2$)$_6$OP(O$_2$)—), was performed as described above (Table 3) except that the final coupling used fluorescein phosphoramidite. The FR-HIVs60mer bound CPG was directly treated with conc. NH$_4$OH at 80° C. for 8 h to give free 5'-FR-HIVs60 mer. Another portion of FR-HIVs60mer bound CPG (2 mg) was deprotected using EDA/EtOH, washed with EtOH, and then treated with phosphodiesterase II according to the procedures described (Gao, X., Zhang, H., and Zhou, X. Method of oligonucleotide purification using enzymes. U.S. patent application Ser. No. 09/364,643). The enzyme purified sequence was cleaved from CPG using NH$_4$OH at 80° C. for 8 h. HPLC (FIG. 10) was performed on a C$_{18}$ reverse phase column (Waters) using 50 mM TEAA in CH$_3$CN. Flow rate was 1 mL/min.

Example 14

This Example describes PCR using the sequences synthesized above. Aliquots of 50 μL of PCR reaction mixture contained 1 pg template DNA strand (1 μL, 30 μM, Ras 99-mer), 11 pmol of each corresponding primer (KB12, 20-mer made on CPG with either stable amide-U linker or regular cleavable succinyl linker), 10 mM of each dNTP (4 μL), and 2 μL Taq enzyme (Promega) in storage buffer. Amplification was carried out for 30 cycles of 90° C. for 30 s, 53° C. for 30 s, and 72° C. for 30 s. Upon completion of the reaction, DNA was purified from the unincorporated dNTPs and the primer with a Clontech purification kit (chroma spin +TE-30) according to the manufacturer's protocol.

The analysis of the PCR products from the two primers (FIG. 11) used 2% agarose gel and TBA buffer. The sequence generated using the stable diol linker without using any separate purification produced the same PCR results as the primers obtained from regular DNA synthesis.

Example 15

This Example describes the derivatization of various surfaces with linking groups.

General Methods

Contact angle measurements. Contact angles were measured by application of static drops (4-10 μL) of deionized water to the substrate surfaces with a micropipetter. The measurements were made visually on both sides of the drops using a Zisman type goniometer. The advancing contact angle, $\theta_a$, was taken as the maximum contact angle observed as the drop size was incrementally increased without an increase in the contact area. The receding contact angle, $\theta_r$, was taken as the minimum contact angle observed as the drop size was decreased with a decrease in the contact area. The average values of a least three measurements performed on each substrate were recorded.

The contact angle measurements were performed using the SCA20 software (DataPhysics Instruments GmbH). Droplet images were acquired with a CCD video camera module (SONY, model XC-77CE). Droplets were dispensed with a Multielectrapette pipette (Matrix technologies).

Imaging of glass plates. After labeling with 4(5)-carboxyfluorescein diisobutyrate, glass plates were treated with ethylene diamine (50% in absolute EtOH) for 15 min, followed by washing with EtOH and acetone and drying using dry $N_2$. The plates were placed on a microscope slide under a cooled CCD camera (Apokee Instruments). The fluorophore was excited and detected at 494 and 525 nm, respectively. The light source was a 200 W Hg—Xe lamp (model 66033, Oriel Instruments). Light exposure time was from 10 to 60 sec. The fluorescent images of the plates were acquired, processed and analyzed using the Image Pro program (Media Imagenics).

Glass derivatization (functionalization of the substrate). Glass plates (22×22 mm$^2$) were cleaned using piranha solution ($H_2SO_4/H_2O_2$, 1:1) for 30 min. After rinsing thoroughly with 18 mΩ water, the plates are carefully rinsed with EtOH 95%, DCM, toluene and dried with a stream of ultra high purity $N_2$.

Glass plates were dipped in a solution of 3-aminopropyltriethoxysilane (43 mM) in toluene heated to 60° C. for 4 min. Following the reaction, glass plates were washed 5 times with toluene and dried with $N_2$.

Fluorescence labeling and quenching issues. Amino groups attached to glass plate surface can be labeled with 4(5)-carboxyfluorescein diisobutyrate and detected by fluorescence emission. However, close proximity of the fluorescent molecules on the flat surface can result in fluorescence quenching. Thus, optimal conditions for fluorescent labeling had to be determined. A glass plate (22×22 mm$^2$) derivatized with 3-aminopropyltriethoxysilane (procedure 1 and 2) was cut in pieces of 3×2 mm$^2$. Each of the pieces were placed in 0.6 mL propylene test tube. Fluorescent labeling was carried out with 100 μL of 4(5)-carboxyfluorescein diisobutyrate with Boc-Gly-OH (a total of 6 μmol for the two species), HOBt (0.91 mg, 6 μmol, prepared from a concentrated solution), and DIC (1 μL, 6 μmol, prepared from a concentrated solution). Boc-Gly-OH was used to compete with 4(5)-carboxyfluorescein diisobutyrate for the coupling with the free amino groups present on the flat substrate. Thus, by varying the ratio of the two reagents (keeping the total concentration of active species constant), the concentration of 4(5)-carboxyfluorescein diisobutyrate on the surface can be diluted. Reactions were carried out for 5 and 60 min (FIG. 1).

High concentration of 4(5)-carboxyfluorescein diisobutyrate induces fluorescence quenching. In the case of glass plates obtained from procedure 1, the mean fluorescence intensity varies linearly with 4(5)-carboxyfluorescein diisobutyrate concentration for concentration as high as 48 mM (80% of 60 mM) for a 5 min reaction time. However, the mean fluorescence intensity drops for the 60 mM 4(5)-carboxyfluorescein diisobutyrate sample. This effect is more critical as the reaction time increases to 60 min. In this case, linearity is conserve for only up to 18 mM (30% of 60 mM) 4(5)-carboxyfluorescein diisobutyrate. This suggests that 4(5)-carboxyfluorescein diisobutyrate density on the surface increases as reaction time increases.

The results appear to be dependent on the glass plate derivatization procedure and on the initial density of 3-aminopropylsilane. When the experiment was reproduced on a glass plate derivatized with 3-aminopropyltriethoxysilane according to procedure 2, linearity is conserved only for concentration of 4(5)-carboxyfluorescein diisobutyrate below 9 mM. Above this concentration, fluorescence quenching occurs and fluorescence intensity drops. In this case, this effect seems to be independent of the reaction time. Therefore, this suggests that 4(5)-carboxyfluorescein diisobutyrate and Boc-Gly-OH coupling to the surface is achieved in high yield within the first five minutes and that increasing the reaction time has little effect on the fluorescent moiety surface density.

Although 3-aminopropyltriethoxysilane is common to the two derivatization procedures, it seems that two different types of surfaces are obtained: one with low reactivity (from procedure 1) and one with high reactivity (from procedure 2). Thus, procedure 2 is suitable for peptide synthesis on glass surface. Furthermore, 4(5)-carboxyfluorescein diisobutyrate (9 mM) diluted with Boc-Gly-OH (51 mM) and reacted for 5 min with the glass plate are optimal conditions for the fluorescent labeling of free amino groups present on the glass plate. It is assumed here that the free amino group surface density is maximum after derivatization and that subsequent peptide synthesis would lead to a density equal or lower to this starting density. However, other factors than density may be involved in the quenching process. It appears for instance that fluorescence emission increases as the distances between the fluorescent moiety and the surface increases.

Example 16

This Example describes the stability of silane bond to chemicals involved in peptide chemistry. Prior to peptide synthesis on the flat solid support, stability of the Si—O—Si bonds towards acidic and basic chemicals involved in peptide chemistry needed to be assessed. A glass plate derivatized from procedure 2 was cut into 3×2 mm$^2$ pieces. Each of the pieces were placed in 0.6 mL propylene test tubes and reacted with a variety of reagents. Following reaction, glass plates were fluorescently labeled according to the conditions described earlier and fluorescent emission was recorded. Reagents tested are summarized in Table 4.

Density control—coupling with a dentrimer can increase the density

TABLE 4

| Glass Plate # | Reagents | Reaction time | Mean Fluorescence Intensity (arbitrary unit) |
|---|---|---|---|
| 1 | TMSOTf (19.5 μL, 107 μmol) TFA (69 μL, 895 μmol) m-cresol (12 μmol, 115 μmol) | 16 h. | 6000 ± 200 |
| 2 | Piperidine (20 μL, 200 μmol) DMF (80 μL) | 16 h | 5900 ± 200 |
| 3 | TEA (10 μL, 71 μmol) DCM (90 μL) | 16 h | 6000 ± 200 |
| 4 | No reagents, for control | | 6100 ± 200 |
| 5 | No reagents, for reproducibility | | 6000 ± 200 |

According to the mean fluorescence intensity measured for each samples, the density of aminopropylsilane on the glass surface is constant. The conditions tested do not seem to induce cleavage of the linker. Peptide synthesis can be carried out without damaging the surface.

Example 17

This Example describes glass derivatization with 11-bromoundecyltrimethoxysilane. Glass plates (22×22 mm$^2$) were cleaned using piranha solution ($H_2SO_4/H_2O_2$, 1:1) for 30 min. After rinsing thoroughly with 18 mΩ water, the plates are carefully rinsed with 95% EtOH, DCM, cyclohexane and dried with a stream of ultra high purity $N_2$.

The glass plates were dipped in a solution of 11-bromoundecyltrimethoxysilane (63.5 μL, 2 mM) in cyclohexane (100 mL) at room temperature for 5, 60, and 270 minutes. Following reaction, glass plates were washed 2 times with cyclohexane, washed with hot cyclohexane (80° C.) for 5 min, rinsed with DCM, acetone, EtOH, and dried with $N_2$.

Example 18

This Example describes in situ modifications.

Azide-terminated linker on solid support. Glass plates containing Bromide terminated $C_{11}$ linker as described above were placed in a supersaturated solution of $NaN_3$ in dry DMF (1.5 g in 100 mL). The solution (together with the undissolved $NaN_3$) was stirred at room temperature. After 24 h the glass plates were rinsed with distilled water.

Amino-terminated linker on solid support. The above azide-terminated glass plates were placed in lithium aluminum hydride solution (0.2 M in THF). After 24 h the glass plates were soaked in THF for an additional 24 h. The glass plates were placed in 5% HCl solution for 5 h to complete hydrolysis of the aluminum complexes, rinsed with deionized water, acetone, and placed in TEA for 10 min in order to convert the terminal —$NH_3^+$ into —$NH_2$.

Example 19

This Example describes cleavage of the linkers from the glass plates. Glass plates samples (3×2 mm$^2$) were treated with $NH_4OH$ (29%, 50 μL) at room temperature, washed with water, 1% TFA in DCM, 10% TEA in DCM, and labeled with diisobutyrate carboxyfluorescein. The experimental contact angles are compared to those described in Heise, A.; Menzel, H.; Yim, H.; Foster, M.; Wieringa, R. H.; Schouten, A. J.; Erb, V; Stamm, M. Grafting of Polypeptides on Solid Substrates by Initiation of N-Carboxyanhydride Polymerization by Amino-Terminated Self-Assembled Monolayers. *Langmuir* 1997, 13, 723-728; and Fryxell, G. E.; Rieke, P. C.; Wood, L. L.; Engelhard, M. H.; Williford, R. E.; Graff, G. L.; Campbell, A. A.; Wiacek, R. J.; Lee, L.; Halverson, A. Nucleophilic Displacements in Mixed Self-Assembled Monolayers. *Langmuir* 1996, 12, 5064-5075.

TABLE 5

| | Contact Angle Measurements | | | |
|---|---|---|---|---|
| Glass | Experimental | | Reported | |
| Plates | Advancing | Receding | Advancing | Receding |
| Br 5' | 76 | 72 | 82 | 77 |
| Br 60' | 75 | 71 | | |
| Br 270' | 81 | 70 | | |
| N3 Br 5' | 75 | 69 | 77 | 71 |
| N3 Br 270' | 78 | 72 | | |
| NH2 Br 5' | 72 | 45 | 63 | 42 |
| NH2 Br 270' | 73 | 44 | | |
| NH2 silane 1 | 70 | 40 | | |
| NH2 silane 2 | 61 | 32 | | |
| NH2 silane 3 | 54 | 28 | | |

$NH_2$ silane 1, 2, and 3 are glass plate samples prepared with 3-aminopropyltriethoxysilane using the same procedure but on different days. Silane 1 was prepared the same day as $NH_2$ Br 270', and contact angle measurements were performed at the same time. The difference between silane 1, 2, and 3 is also attributed to aging of the glass plates (the time that separates derivatization and contact angle measurement, this is also linked to the storage conditions of the glass plates: dry in contact with the air, or kept in solution. Silane 1 was dried after derivatization, contact angle was measured 1 h later. Silane 2 was dried after derivatization, contact angle was measured 10 h later. Silane 3 was kept in toluene after derivatization, and the contact angle was measured 10 h later. There are no significant differences between the contact angle of $NH_2$ silane 1 and $NH_2$ Br 270'.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, chemistry or related fields are intended to be within the scope of the following claims.

What is claimed is:

1. A method of generating purified oligonucleotides comprising:

a) providing:

i) a substrate comprising an array of oligonucleotides attached to said substrate via anchor moieties attached to non-cleavable linkers attached to said substrate, wherein said anchor moieties comprise the structure —C(X)—C(Y), wherein X comprises —OPO$_2$O—, Y is a nucleophile and wherein said structure is part of a ring moiety;

ii) a deprotecting solution; and iii) and a wash solution;

b) deprotecting said oligonucleotides with said deprotecting solution;
c) washing said oligonucleotides with said wash solution; and
d) cleaving said oligonucleotides at said anchor moieties to provide purified oligonucleotides.

2. The method of claim 1, wherein said deprotecting solution comprises ethyl diazoacetate (EDA) in ethanol.

3. The method of claim 1, wherein said anchor moieties are attached to said noncleavable linkers via a 5'-O—P— linkage.

4. The method of claim 1, wherein said anchor moieties are attached to said oligonucleotides via a 3'-O—P—O-3' phosphodiester attachment.

5. The method of claim 1, wherein said cleaving comprises cleavage selected from the group consisting of chemical cleavage and enzymatic cleavage.

6. The method of claim 5, wherein said chemical cleavage comprises exposure to ammonium hydroxide.

7. The method of claim 5, wherein said enzymatic cleavage comprises exposure to a ribonuclease.

8. The method of claim 7, wherein said ribonuclease is selected from the group consisting of RNase A, $T_1$, and $U_2$.

9. The method of claim 7, wherein said ribonuclease cleaves said anchor 3'-O—P—O-3' nucleotide phosphodiester attachments.

10. The method of claim 1, wherein said oligonucleotides are further purified utilizing liquid chromotography.

11. The method of claim 1, wherein said oligonucleotides are further purified utilizing gel purification.

12. The method of claim 1, wherein said oligonucleotides comprise deoxyribonucleic acid.

13. The method of claim 1, wherein said oligonucleotides comprise ribonucleic acid.

14. The method of claim 1, wherein said oligonucleotides comprise a label.

15. The method of claim 14, wherein said label comprises a fluorescent label.

16. The method of claim 1, wherein said anchor moieties comprise ribose nucleotides.

17. Purified oligonucleotides generated according to the method of claim 1.

18. The oligonucleotides of claim 17, wherein said oligonucleotides comprise deoxyribonucleic acid.

19. The oligonucleotides of claim 17, wherein said oligonucleotides comprise ribonucleic acid.

* * * * *

SEQUENCE LISTING

<160> NUMBER OF SEQ ID NOS: 7

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
tatgtagcct cggtc                                                    15

<210> SEQ ID NO 2

-continued

```
<211> LENGTH: 16
<212> TYPE: DNA
<213> ORGANISM: Artificial Sequence
<220> FEATURE:
<223> OTHER INFORMATION: Synthetic

<400> SEQUENCE: 2
ctcctacggg aggcag                                                          16

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
gtcaccatgt tgactcacca tgtc                                                 24

<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4
tgttgactca ccatgtcgtc accatgttga ctcaccatgt c                              41

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tctattgttg gatcatattc                                                      20

<210> SEQ ID NO 6
<211> LENGTH: 60
<212> TYPE: DNA
<213> ORGANISM: Artificial Sequence
<220> FEATURE:
<223> OTHER INFORMATION: Synthetic

<400> SEQUENCE: 6
tggaaagata cctaaaggat caacagctcc tggggatttg gggttgctct ggaaaactct          60

<210> SEQ ID NO 7
<211> LENGTH: 60
<212> TYPE: DNA
<213> ORGANISM: Artificial Sequence
<220> FEATURE:
<223> OTHER INFORMATION: Synthetic

<400> SEQUENCE: 7
tggaaagata cctaaaggat caacagctcc tggggatttg gggttgctct ggaaaactct          60
```